(12) United States Patent
Medina et al.

(10) Patent No.: US 8,828,311 B2
(45) Date of Patent: Sep. 9, 2014

(54) RETICULATED MESH ARRAYS AND DISSIMILAR ARRAY MONOLITHS BY ADDITIVE LAYERED MANUFACTURING USING ELECTRON AND LASER BEAM MELTING

(75) Inventors: Frank Medina, El Paso, TX (US); Lawrence Murr, El Paso, TX (US); Ryan Wicker, El Paso, TX (US); Sara Gaytan, Chihuahua (MX)

(73) Assignee: Board of Regents, The University of Texas System, Austin, TX (US)

( * ) Notice: Subject to any disclaimer, the term of this patent is extended or adjusted under 35 U.S.C. 154(b) by 1096 days.

(21) Appl. No.: 12/780,005

(22) Filed: May 14, 2010

(65) Prior Publication Data

US 2010/0291401 A1 Nov. 18, 2010

Related U.S. Application Data

(60) Provisional application No. 61/178,903, filed on May 15, 2009.

(51) Int. Cl.
*B23K 26/34* (2014.01)
*B23K 15/00* (2006.01)

(52) U.S. Cl.
CPC ............ *B23K 26/34* (2013.01); *B23K 15/0086* (2013.01)
USPC .......... 419/2; 428/593; 428/594; 219/121.66; 419/5; 419/10; 419/26

(58) Field of Classification Search
USPC ............................................. 419/2
See application file for complete search history.

(56) References Cited

U.S. PATENT DOCUMENTS

| | | | | |
|---|---|---|---|---|
| 5,490,882 A | * | 2/1996 | Sachs et al. | 134/1 |
| 5,520,738 A | * | 5/1996 | Aindow et al. | 118/621 |
| 6,519,500 B1 | * | 2/2003 | White | 700/119 |
| 2005/0169893 A1 | * | 8/2005 | Koblish et al. | 424/93.7 |
| 2007/0151961 A1 | | 7/2007 | Kleine et al. | |
| 2009/0035448 A1 | | 2/2009 | Flanagan et al. | |
| 2009/0221898 A1 | | 9/2009 | Hillis et al. | |

OTHER PUBLICATIONS

Atamert, S., et al., "Comparison of the Microstructures and Abrasive Wear Properties of Stellite Hardfacing Alloys Deposited by Arc Welding and Laser Cladding," Metallurgical Transactions A, vol. 20A, Jun. 1989, pp. 1037-1054.
Davis, N.G., et al., "Solid-State Foaming of Titanium by Superplastic Expansion of Argon-Filled Pores," J. Mater. Res., vol. 16, No. 5, May 2001, pp. 1508-1519.

(Continued)

*Primary Examiner* — Jessee Roe
*Assistant Examiner* — Christopher Kessler
(74) *Attorney, Agent, or Firm* — Edwin S. Flores; Chalker Flores, LLP

(57) ABSTRACT

Compositions and methods for making a three dimensional structure comprising: designing a three-dimensional structure; melting the three-dimensional structure from two or more layers of a metal powder with a high energy electron or laser beam is described herein. The position where the metal is melted into the structure is formed along a layer of metal powder, wherein the location and intensity of the beam that strikes the metal layer is based on the three-dimensional structure and is controlled and directed by a processor. The instant invention comprises a novel dry state sonication step for removing metal powder that is not melted from the three dimensional structure.

28 Claims, 31 Drawing Sheets

(56) References Cited

OTHER PUBLICATIONS

Dunand, David C "Processing of Titanium Foams," Advanced Engineering Materials, (2004), vol. 6, No. 6, pp. 369-376.

Garcia, A. de J. Saldivar, et al., "Formation of Hcp Martensite During the Isothermal Aging of an Fcc Co—27Cr—5Mo—0.05C Orthopedic Implant Alloy," Metallurgical and Materials Transactions A, vol. 30A, May 1999, pp. 1177-1184.

Gaytan, S.M., et al., "Advanced Metal Powder Based Manufacturing of Complex Components by Electron Beam Melting," Materials Technology, (2009), vol. 24, No. 3, pp. 180-190.

Heinl, Peter, et al., "Cellular Ti—6Al—4V Structures with Interconnected Macro Porosity for Bone Implants Fabricated by Selective Electron Beam Melting," Acta Biomaterials, (2008), vol. 4, pp. 1536-1544.

Huang, Ping, et al., "Strain Induced E-Martensite in a Co—Cr—Mo Alloy: Grain Size Effects," Materials Letters, May 1999, vol. 39, pp. 244-248.

Lefebvre, Louis-Philippe, et al., "Porous Metals and Metallic Foams: Current Status and Recent Developments," Advanced Engineering Materials, (2008), vol. 10, No. 9, pp. 775-787.

Li, Qizhen, et al., "Mechanical Properties of Cast Ti—6Al—4V Lattice Block Structures," Metallurgical and Materials Transactions A, Feb. 2008, vol. 39A, pp. 441-449.

Meacock, C.G., et al., "Structure and Properties of a Biomedical Co—Cr—Mo Alloy Produced by Laser Powder Microdeposition," Journal of laser Applications, May 2009, vol. 21, No. 2, pp. 88-95.

Moyen, BJ, et al., "Effects on Intact Femora of Dogs of the Application and Removal of Metal Plates. A Metabolic and Structural Study Comparing Stiffer and More Flexible Plates," J. Bone Joint Surg. Am., (1978), vol. 60, pp. 940-947.

Murr, L.E., et al., "Microstructure and Mechanical Behavior of Ti—6Al—4V Produced by Rapid-Layer Manufacturing, for Biomedical Applications," Journal of the Mechanical Behavior of Biomedical Materials, (2009), vol. 2, pp. 20-32.

Murr, L.E., et al., "Characterization of Ti—6Al—4V Open Cellular Foams Fabricated by Additive Manufacturing Using Electron Beam Melting," Mater. Sci. Engng., (2009), pp. 1861-1868.

Murr, L.E., et al., Microstructured and Mechanical Properties of Electron Beam-Tapid Manufactured Ti-6Al-4FV Biomedical Prototypes Comparedto Wrought Ti-6Al44V, Materials Characterization, (2009), vol. 60, pp. 96-105.

Murr, Lawrence E., et al., "Metallographic Characterization of Additive-Layer Manufactured Products by Electron Beam Melting of Ti—6Al—4V Powder Metallographische charakterisierung von Halbzuegen Mit Additiveschichten Hergestellt Durch Elektronenstrahlschmelzen Von Ti—6Al—4V Pulver," Prakt. Metallogr. (2009), vol. 46, pp. 442-453.

Oh, Ik-Hyun, et al., "Mechanical Properties of Porous Titanium Compacts Prepared by Powder Sintering," Scripta Materilia, (2003), vol. 49, pp. 1197-1202.

Shin, Jong-Choul, et al., "Effect of Molybdenum on the Microstructure and Wear Resistance of Cobalt-Base Stellite Hardfacing Alloys," Surface and Coatings Technology, (2003), vol. 166, pp. 117-126.

\* cited by examiner

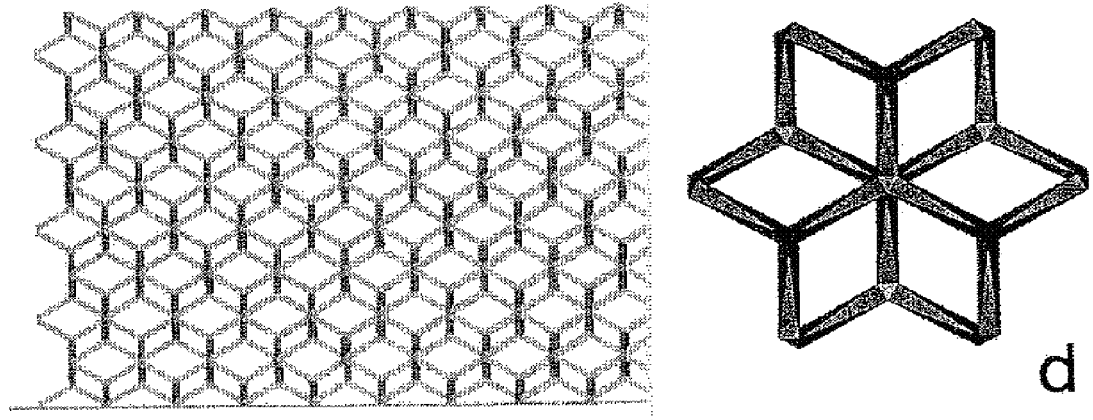
*FIG. 5D*
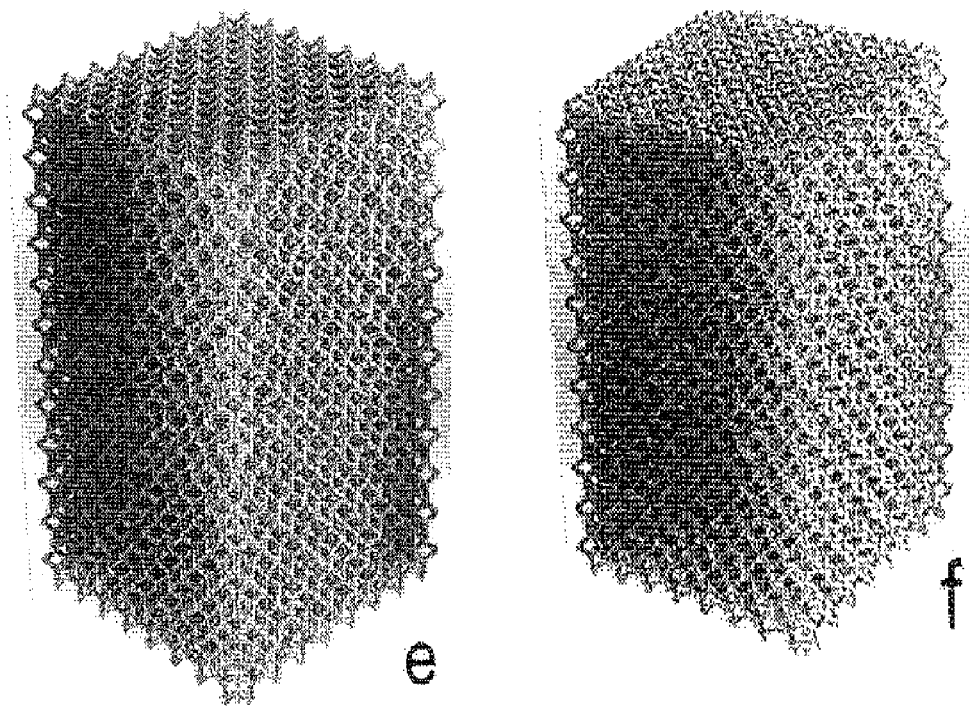
*FIG. 5E*  *FIG. 5F*

RETICULATED MESH ARRAYS AND DISSIMILAR ARRAY MONOLITHS BY ADDITIVE LAYERED MANUFACTURING USING ELECTRON AND LASER BEAM MELTING

CROSS-REFERENCE TO RELATED APPLICATIONS

This application claims priority to U.S. Provisional Application Ser. No. 61/178,903 filed May 15, 2009, the entire contents of which are incorporated herein by reference.

TECHNICAL FIELD OF THE INVENTION

The present invention relates in general to the field of mesh arrays and monoliths, and more particularly, to the fabrication of complex, multifunctional metal cellular and foam and reticulated mesh arrays and dissimilar array monoliths by additive layered manufacturing using electron and laser beam melting.

STATEMENT OF FEDERALLY FUNDED RESEARCH

None.

BACKGROUND OF THE INVENTION

Without limiting the scope of the invention, its background is described in connection with medical implants.

Over the past decade, the number of load-bearing and non-load-bearing or low-load-bearing metal or alloy implants for biomedical applications has increased dramatically, with current estimates in the millions worldwide. These include orthopedic joint implants, rods, bone plates, and varieties of maxillofacial or craniofacial replacements [1,2]. In load-bearing implant cases, in particular, biomechanical mismatch between the implant and the surrounding bone often leads to inhomogeneous stress transfer or so-called stress-shielding phenomena. This often leads to stress concentration by bone remodeling and retarded bone healing [3,4] which can lead to loosening and subsequent revision surgery. Revision surgeries are often more complicated than the original surgery, and most individuals can only undergo a few such surgeries. Mechanical biocompatibilities require strong, light-weight, low modulus of elasticity (or Young's modulus), non-toxic metals or alloys. However, even implants with a low elastic modulus similar to bone may not alleviate loosening because there may be no provision for bone tissue ingrowth. Bone consists of an outer cortical shell with an elastic modulus ranging from 18 to 20 GPa and a density of roughly 1.9 g/cm$^3$, in contrast to the inner (medullary) trabecular bone which is a highly porous, reticulated structure with roughly 55 to 70 percent interconnected porosity (or roughly 1.3 to 2.0 g/cm$^3$ density) [5]. Cell penetration and tissue ingrowth requires an interconnected pore system with pore diameters in excess of 0.1 mm [6,7]. This is especially true for non-load-bearing craniofacial implants. Consequently porous metal implants can provide for tissue ingrowth as well as more homogeneous stress transfer for load-bearing implant applications based upon model predictions for open cellular materials by Gibson and Ashby [8]:

$$E = E_o (\rho/\rho_o)^n, \quad (1)$$

where, E and $E_o$ are the elastic (Young's) moduli of the cellular (foam) and fully dense material, respectively, $\rho$ and $\rho_o$ are the corresponding porous and bulk densities, and n has values ranging from 1.8 to 2.2 [9].

Open-cell titanium and titanium alloy structures have been fabricated by a number of solid-state processes: controlled powder sintering (including hollow powder sintering), gas expansion followed by sintering, polymeric foam replication, etc. [10-12]. Cellular lattices, lattice-truss structures or lattice-block structures (three-dimensional-periodic reticulated materials, especially cast Ti-6Al-4V lattice-block structures) have recently been described by Li, et al. [14], while Heinl, et al. [15] have described cellular Ti-6Al-4V structures for bone implants fabricated by selective electron beam melting.

United States Patent Application No. 20070151961 (Kleine and Gale, 2007) disclose methods and systems for laser machining a substrate in the fabrication of an implantable medical device. The Kleine invention relates to laser machining of implantable medical devices such as stents. Laser machining refers to removal of material accomplished through laser and target material interactions. Generally speaking, these processes include laser drilling; laser cutting; and laser grooving, marking, or scribing. Laser machining processes transport photon energy into a target material in the form of thermal energy or photochemical energy. Material is removed by melting and blowing away, or by direct vaporization/ablation.

A method of producing a customized surgical tool, comprising the steps of obtaining image data corresponding to a patient body region, processing the image data to produce fabrication data; and rapid prototyping the customized surgical tool according to the fabrication data is taught in United States Patent Application No. 20090221898 (Hillis, et al., 2009). m\Many technologies may be implemented as the rapid prototyping machine in the Hillis invention, for example, Stereolithography, Fused Deposition Modeling, and/or Electron Beam Melting.

United States Patent Application No. 20090035448 (Flanagan and O'Connor, 2009) describe a method of making a medical device with a porous coating, the method comprising: providing a workpiece sized to fit within lumens of the body, the workpiece having an accessible surface; positioning a nozzle adjacent the accessible surface; ejecting a coating material from the nozzle toward the accessible surface; directing a laser beam toward the coating material ejected from the nozzle, thereby melting the coating material with the laser; allowing the melted coating material to cool and form a porous coating on the workpiece; and loading the porous coating with a therapeutic agent.

SUMMARY OF THE INVENTION

The present invention includes compositions and methods for the fabrication of reticulated solid-mesh structures and monolithic solid/mesh biomedical implant and functionally graded monoliths by electron beam melting (EBM). These layer-built components fabricated by CAD-driven EBM from precursors comprising Ti-6Al-4V or Co-26Cr-6Mo-0.2C powder. The structure(s) can be characterized by optical and/or scanning electron microscopy. A novel and innovative step of removing powder that is not melted from the fabricated devices comprising a dry state sonication is also disclosed herein.

In one embodiment, the present invention includes compositions and methods of making a three dimensional structure comprising: designing a three-dimensional structure; melting the three-dimensional structure from two or more layers of a metal powder with a high energy electron beam, wherein the position where the metal is melted into the structure is formed along a layer of metal powder, wherein the location and intensity of the beam that strikes the metal layer is based on the three-dimensional structure is controlled and directed by a processor and removing metal powder from the three-dimensional structure that is not melted. The method as disclosed herein further comprises the step of removing the metal powder. The removal of the metal powder that is not melted is achieved by, contacting the metal powder that is not melted with one or more ultrasonic devices and removing the metal powder that is not melted by sonication using the one or more ultrasonic devices, wherein the sonication is a dry sonication.

The one or mole ultrasonic devices used for the purposes of removal of the metal powder that is not melted are selected from the group consisting of resonant probes, ultrasonic welders or related high frequency sound transmission devices. Specifically, in the instant invention the ultrasonic device used is a resonant probe, operated at frequencies ranging from 20 to 80 kHz. Typically, the frequency of operation of the one or more ultrasonic device is dependent on a shape, a density, and geometry of the three-dimensional structure.

In one aspect, the three dimensional structure comprises at least a portion is a reticulated mesh array. In another aspect, the electron beam melts metal powder layers using electron or laser beams. In a specific aspect, the metal powder comprises Ti-6Al-4V or Co-26Cr-6Mo-0.2C. In yet another aspect, the three dimensional structure comprises at least one of a porous coating, a thin porous bead coating, a sintered mesh arrays, a thermal-spray coating, and a metallic foam on a medical device. In another aspect, the method further comprises the steps of obtaining three-dimensional coordinates for a shape for tissue replacement, calculating the shape of a three-dimensional implant based on the three-dimensional coordinates of the shape for tissue replacement, and forming the three-dimensional implant. In yet another aspect, the method further comprises the steps of obtaining three-dimensional coordinates for a shape for tissue replacement, calculating the shape of a three-dimensional implant based on the three-dimensional coordinates of the shape for tissue replacement, and selecting one or more metal powders to form the three-dimensional implant based on at least one of weight, mechanical strength, porosity, geometry and biocompatibility. In one aspect, the method further comprises the step of adding one or more biocompatible polymers to the three dimensional structure. In another aspect, the method further comprises the step of adding one or more cellular growth factors. In yet another aspect the three dimensional structure comprises orthopedic implants, femoral stems, tibial stems, femoral rods, and combinations and modifications thereof.

In another embodiment the invention includes a three dimensional, structure made by the method described hereinabove, e.g., a biologically compatible, three dimensional, reticulated mesh array.

In yet another embodiment, the present invention includes a method of making a biologically compatible, three dimensional, reticulated mesh array comprising: designing a three-dimensional reticulated mesh array structure comprising lattice elements; melting the three-dimensional reticulated mesh array structure from two or more layers of a biocompatible metal powder with a high energy electron beam, wherein the position where the metal is melted into the structure is formed along a layer of metal powder, wherein the location and intensity of the beam that strikes the metal layer is based on the three-dimensional structure is controlled by and directed by a processor; and removing metal powder from the three-dimensional structure that is not melted.

The method for making a biologically compatible, three dimensional, reticulated mesh array as disclosed hereinabove in the instant invention further comprises the steps of removing the metal powder that is not melted by, contacting the metal powder that is not melted with one or more ultrasonic devices and removing the metal powder that is not melted by sonication using the one or more ultrasonic devices, wherein the sonication is a dry state sonication. The one or mole ultrasonic devices used hereinabove consist of resonant probes, ultrasonic welders or related high frequency sound transmission devices. In a specific aspect the ultrasonic device used in the instant invention is a resonant probe operated at frequencies ranging from 20 to 80 kHz. The operational frequencies for the selected ultrasonic devices are dependent on a shape, a density, and geometry of the three dimensional reticulated mesh array.

In one aspect, the three dimensional structure is a reticulated mesh array. In another aspect, the electron beam melts metal powder layers using electron or laser beams. In a specific aspect, the metal powder comprises Ti-6Al-4V or Co-26Cr-6Mo-0.2C. In yet another aspect, the three dimensional structure comprises at least one of a porous coating, a thin porous bead coating, a sintered mesh array, a thermal-spray coating, and a metallic foam on a medical device. In another aspect, the method further comprises the steps of obtaining three-dimensional coordinates for a shape for tissue replacement, calculating the shape of a three-dimensional implant based on the three-dimensional coordinates of the shape for tissue replacement, and forming the three-dimensional implant. In another aspect, the method further comprises the steps of obtaining three-dimensional coordinates for a shape for tissue replacement, calculating the shape of a three-dimensional implant based on the three-dimensional coordinates of the shape for tissue replacement, and selecting one or more metal powders to form the three-dimensional implant based on at least one of weight, mechanical strength, porosity, geometry and biocompatibility. In yet another aspect, the method further comprises the step of adding one or more biocompatible polymers to the three dimensional structure. In another aspect, further comprises the step of adding one or more cellular growth factors. Finally, in one aspect the method comprises the optional step of annealing and polishing the biologically compatible, three dimensional, reticulated mesh array.

In one embodiment the instant invention describes a biologically compatible, three dimensional, mesh array made by the method disclosed hereinabove.

BRIEF DESCRIPTION OF THE DRAWINGS

For a more complete understanding of the features and advantages of the present invention, reference is now made to the detailed description of the invention along with the accompanying figures and in which:

(FIG. 1C) shows an SEM image for a mesh build, and (FIG. 1D) optical micrograph for mesh build in FIG. 1C;

(FIG. 2A) Cylindrical mesh, (FIG. 2B) Hemispherical mesh showing geometrical arrays at 45° when viewed horizontally along 1 and 2 as shown in FIG. 2C;

FIGS. 3A-3E are examples of EBM implant prototypes. (FIG. 3A) Top end of adult human femur (From Wikipedia Commons), FIGS. 3B and 3C are cylindrical (intramedullary) rod/mesh CAD examples, FIG. 3D shows a CAD end section for FIG. 3B but with solid (fully dense) core, and FIG. 3E Tibial knee stem prototype (exaggerated): EBM built Ti-6Al-4V;

(FIGS. 4A and 4B) 2× base foam or starting build unit, (FIG. 4B) 3× base foam, FIGS. 4C and 4D show 3D test blocks CAD element corresponding to FIGS. 4A and 4B respectively. Base foam porosity—6 PPI. Measured densities corresponding to FIGS. 4A and 4B are 0.83 g/cm$^3$ and 0.58 g/cm$^3$;

FIGS. 5A-5F show CAD model views and EBM fabricated prototypes utilizing the Materialize™ dode-thin software/CAD element;

FIGS. 6A-6C show 3D, 3D half-section, and end views, respectively;

FIGS. 7A to 7C show 3D, 3D half section, and end views, respectively;

(FIG. 8A) shows Ti-6Al-4V foams with increasing density left-to-right, (FIG. 8B) shows enlarged views of foams with closed or solid ligaments (left) and open ligaments (right), (FIG. 8C) shows schematic views of closed or solid ligament cross-section (left) and open ligament cross section (right);

(FIG. 9A) precursor powder in the SEM, (FIG. 9B) powder particle size distribution (histogram), (FIG. 9C) EDS spectrum showing qualitative composition of the powder;

(FIG. 10A) rectangular and cylindrical Co—Cr—Mo components built in the EBM system illustrated in FIG. 1A, (FIG. 10B) shows tensile specimens machined from cylindrical components shown in FIG. 10A. Tested and fractured tensile specimens in FIG. 10B are shown in FIG. 10C. The arrow in FIG. 10A indicates the EBM build direction;

(FIG. 18A) irregular $Cr_{23}C_6$ carbides in the fcc Co matrix and (FIG. 16B) similar carbide concentrations in a grain boundary (arrows) in. Note overlapping stacking faults in both 18A and 18B;

FIGS. 19A and 19B show outer and inner views. The larger arrow (right) in FIG. 19B indicates the build direction while the small arrow to the left indicates the sectioning of the component for examination.

(FIG. 20A) shows a lower magnification image with the build direction (at arrow) corresponding to that shown in FIG. 19B, (FIG. 20B) shows a magnified view showing variations of carbide ($Cr_{23}C_6$) arrays and columnar strings;

(FIG. 22A) shows an equiaxed, fcc grain structure containing annealing twins with fine carbides ($Cr_{23}C_6$) at some grain boundaries, (FIG. 22B) shows a preferential carbide etch at high energy grain boundary segments;

FIGS. 24A and 24B are TEM bright-field image comparison for: (FIG. 24A) the annealed and polished femoral knee component and (FIG. 24B) the horizontal plane for the as-fabricated cylindrical component. (FIG. 24A) shows stacking faults on non-concurrent {111} planes and FIG. 24B shows irregular $Cr_{23}C_6$ carbides and stacking faults;

(FIG. 26A) rectangular mesh component, (FIG. 26B) SEM image for a side section in FIG. 26A showing mesh strut structure, (FIG. 26C) EDS spectrum showing qualitative composition of the mesh structures in (FIG. 26B);

(FIG. 26A) carbide arrays in the horizontal plane (perpendicular to the cylinder axis and EBM build direction); (FIG. 26B) corresponding fracture surface. Arrows show fracture surface features corresponding to carbide arrays in FIG. 28A.

DETAILED DESCRIPTION OF THE INVENTION

Figure 1A:
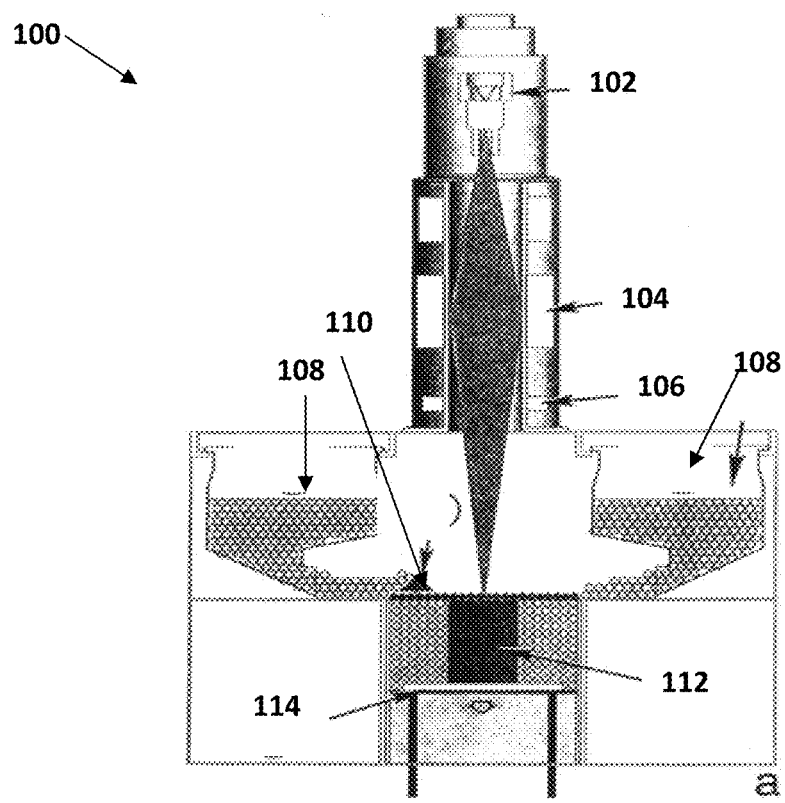
FIGS. 1A-1D show an EBM system schematic (FIG. 1A) and build structures and microstructures (FIGS. 1B-1D), (FIG. 1B) shows an optical micrograph for a standard build.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The term "three-dimensional structures" and the like as used herein refer generally to intended or actually fabricated three-dimensional configurations (e.g. of structural material or materials) that are intended to be used for a particular purpose. Such structures, etc. may, for example, be designed with the aid of a three-dimensional CAD system. The term "monolithic device" as used herein refers to a device formed on a single substrate.

The term "electron beam" as used herein in various embodiments refers to any charged particle beam. The sources of the charged particle beam can include an electron gun, a linear accelerator and so on. The term "laser beam" as described herein is defined as a path of any radiation originating at a laser and being transmitted through passing through either fiber or air. The laser beam actually includes two laser beam portions: an incident laser beam portion and a return (reflected) laser beam portion.

The term "biocompatible polymer" as used herein will be understood to refer to a polymer which is non-toxic to the recipient and also presents no deleterious or untoward effects on the recipient's body, such as an immunological reaction at the injection site. The definition also includes that the degradation products of the polymer must also be non-toxic and presents no deleterious or untoward effects. A suitable biocompatible polymer when in contact with the human body is not toxic nor injurious to the person, and does not cause an immunological response, and include for example, silicone and silicone-based polymers; polytetrafluoroethylene (ePTFE); a natural hydrogel; a synthetic hydrogel; TEFLON (polytetrafluoroethylene); silicone, polyurethane; polysulfone; cellulose; polyethylene; polypropylene; polyamide; polyester; and a combination of two or more of these materials. Examples of natural hydrogels include fibrin, collagen, elastin, and the like. polyethylene terephthalate (PET), polyurethane urea and silicone.

The term "cellular growth factor" as used herein refers to those compounds other than the anabolic hormones which may be optionally added to the formulations for their known benefits in stimulating the growth and elaboration of cells. Examples include, epithelial growth factor (EGF), platelet derived growth factor (PDGF), transforming growth factor (TGF) and insulin-like growth factor (IGF), among others.

As used herein the term "implant" generally refers to a surgically implanted structure or device, such as a dental implant a subcutaneous implant, or a prosthesis. The term also includes artificial organs, for example artificial kidneys, vessels, skin substitute, artificial eye lenses, so-called intraocular lenses, dental prostheses and also contact lenses.

The present invention involves methods for building complex, multifunctional metal cellular and foam arrays as well as mesh arrays and foam or mesh array complexes and/or solid-fully dense composites consisting of cellular, foam, or mesh arrays and solid segments built as monoliths, from metal powders, by additive-layered (AM) manufacturing. The manufacturing method melts metal powder layers using electron or laser beams. These layer-built monoliths can emulate bone and have numerous orthopedic or bone replacement strategies. Furthermore, directed stress or controlled stiffness (elastic modulus) structures for impact energy absorption and related light-weight structural components for aeronautic, aerospace and automotive applications are fabricated from CAD models or from CT-sans replicated in CAD models. Orthopedic implants, including femoral and tibial stems, femoral rods etc. can be built specific to patients from CT-scan-CAD models. Common metal powder products can be built from Ti, Ti-6Al-4V, Co-26Cr-6Mo, and stainless steel powders, or from any metal or alloy powder. Functional monoliths can include cortical bone density arrays surrounding a lower density, trabecular or medullary array having porosity able to alloy bone tissue ingrowth and vascular system growth.

A novel feature of the fabrication method of the method of the instant invention is a process for powder removal that involves the use of contact ultrasonic devices. Resonant probe tips ranging from roughly 20 to 80 kHz can be used with different mesh or foam component densities. These devices are used in the dry state—the component or product is not submerged in any liquid medium for sonication. The powder removal sonication method of the instant invention has been demonstrated to be successful for open structures as fine as 1 mm or less, depending upon the geometrical complexity of the foam or mesh arrays and the complexity of the functionally graded monolithic product. This process is a critical step for creating functional foam or mesh components or products by electron or laser beam melting for additive manufacturing.

Some specific aeronautical/aerospace applications include: Impact energy management-landing gear assemblies; Blast/shock wave production; Sound absorption—vibration suppression; Thermal management—heat transfer/heat exchange; High damping capability and stiffness applications in turbine engine structural parts; Structural component stress (mechanical property) isotropy; Ballistic penetration/armor innovations: multi-function armor regimes: monolithic fabrication.

Porous coatings, notably thin, porous bead coatings, sintered mesh arrays, thermal-spray coatings and metallic foams have been incorporated into biomedical devices and appliances for several decades to improve bone compatibility, stability, and bone ingrowth. This invention demonstrates the fabrication of reticulated mesh arrays as integral components of monolithic products using Ti-6Al-4V powder to build complex, 3D structures by electron beam melting (EBM). Using software capable of building lattice-truss or cellular lattices with high symmetry, 3D-periodic reticulated arrangements such as hip stem and knee component prototypes have been fabricated with complete mesh arrays or with solid stems with a surrounding mesh structure completely fabricated as a monolithic product. The 3D mesh structures begin with so-called lattice elements which can be designed, computed, and attached to a CAD program for additive layered manufacturing by EBM. Mesh arrays with cortical bone density (1.9 g/cm$^3$) can be fabricated with various lattice-truss structures and truss dimensions tailored to stress-strain and stiffness properties to optimize porous bone-replacement implants, including craniofacial replacements, etc. Mesh-to-mesh structures and functionally graded structures are also explored. Metallographic analysis of these structures using optical and electron microscopies illustrate their microstructural characteristics in association with measured mechanical properties such as microindentation hardness which can be related linearly to residual stress.

CASE STUDY I—Reticulated solid-mesh structures and monolithic solid/mesh implants by electron or laser beam melting of Ti-6Al-4V powder.

FIG. 1A illustrates the ARCAM-EBM system used to manufacture the arrays of the present invention. This system operates at an accelerating voltage of 60 kV to raster a focused electron beam over a Ti-6Al-4V powder layer sequentially raked from cassettes which gravity feed the powder onto the layer-building component. The electron beam initially scans each powder layer at ~15,000 mm/s in multiple passes to preheat the layer to ~640° C. The melt scan is driven by a CAD program at 400 mm/s at reduced beam current. Processing of the layer-built component occurs in a vacuum of $10^{-4}$ Torr and a helium gas bleed at the building component of $10^{-2}$ Torr to facilitate cooling and thermal stability. The Ti-6Al-4V powder utilized in this research had a nominal composition of 6% Al, 4% V, 0.13% O and the balance Ti by weight (ASTM Grade 5). The average (or mean) atomized powder diameter was ~30 µm, with a size distribution extending to >100 µm. Layer thicknesses were ~100 µm.

To build reticulated mesh arrays and monolithic prototypes composed of mesh arrays connected to solid components (including functionally graded mesh components), the inventors utilized several software packages. These included Solidworks™ Software (solidworks.com) and Materialise/Magics™ Software (materialise.com) along with Selective Space Structure (3S) software from FIT-Fruth Innovative Technologien GmbH. These software packages generate 3D structures which can be attached to individual (solid) parts. These 3D structures are based on lattice or structure units. In the 3S software a structural drawing is used to define cell ranges and cell descriptions where the structure definition of the cell is made in the 3S Generator. The 3S Generator was used to build up a cell from simple design elements such as nodes and trusses or import sti-files of more complex cell designs. Density variations can be achieved in any mesh design by varying the truss dimensions (diameter and spacing) and geometries. Functional grading can be achieved by varying these dimensional parameters over a spatial regime extending from a fully dense Ti-6Al-4V section (4.43 g/cm$^3$) to some fractional density.

The mesh and monolithic devices made using the present invention were characterized by optical metallography and scanning electron microscopy. Specimen sections were mounted and polished and etched with a solution consisting of 100 mL H$_2$O, 2.5 mL HF and 5 mL HNO$_3$. A digital imaging Reichert MEF4 A/M optical metallograph was used for optical metallography. Electron microscopy was performed in a Hitachi S4800 field emission scanning electron microscope (FESM) which also included elemental analysis using an EDAX microscope energy-dispersive X-ray spectrometer.

Hardness testing of EBM-built components was performed in a Shimadzu HMW-2000 microindentation (Vickers) hardness (HV) tester using 25 gf (0.25 N) loads for mesh-truss measurements and 100 gf (1 N) loads for solid, fully dense component measurements.

Figure 1B:
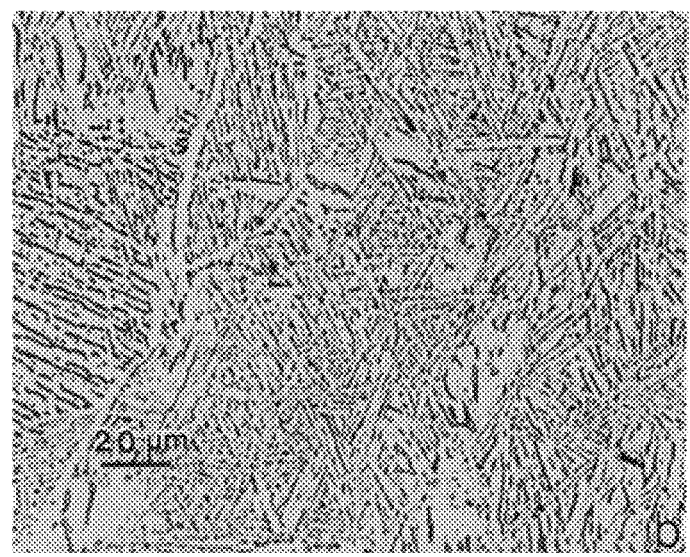
Figure 1C:
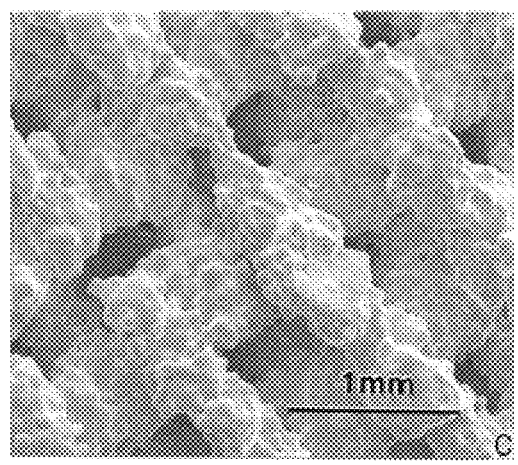
Figure 1D:
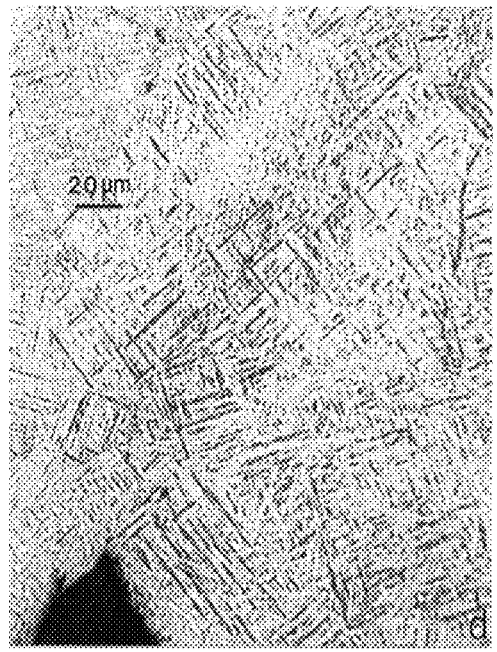

FIG. 1A shows a schematic view of the Arcam A2 EBM system 100. The schematic of FIG. 1A illustrates an electron beam-forming system 100 similar to a scanning electron microscope (SEM) or an electron beam welding facility which consists generally of an electron gun 102 and an electron beam focusing (electromagnetic) lens system 102 with included beam scan coils. The electron beam accelerating potential of 60 kV along with an optimized beam current and focus during layer melting produces an energy density of ~102 kW/cm2. The Ti-6Al-4V or a similar powder is fed from cassettes marked 108 and raked into ~100 µm layers at 110. The building component 112 is lowered on the build table 114 with each layer. FIG. 1B shows the acicular α (hcp)-microstructure for a simple cylindrical (solid) build while FIGS. 1C and 1D show a mesh structure and its corresponding α' (hcp-martensite) microstructure. The normal (solid) build Vickers microindentation hardness was measured to average between 3.6 GPa and 4.3 GPa, while the average mesh-strut microindentation hardness (FIGS. 1C and 1D) averaged 4.8 GPa as a consequence of more rapid cooling.

Figure 2A:
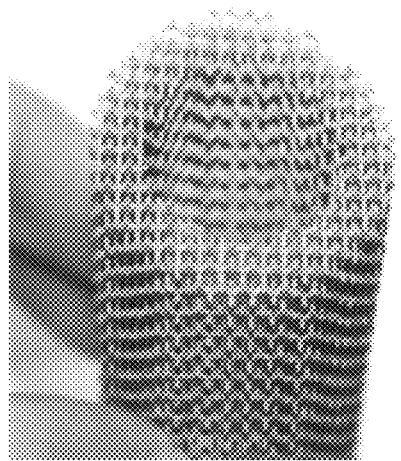
FIGS. 2A-2C show two Ti-6Al-4V mesh arrays.
Figure 2B:
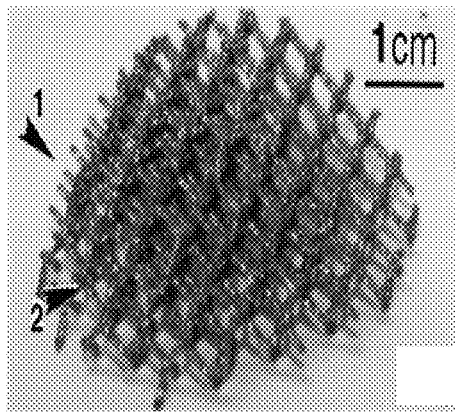
Figure 2C:
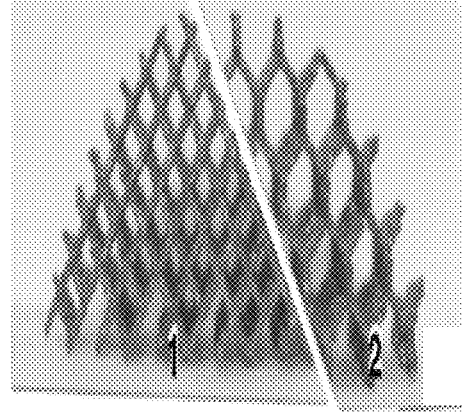
Figure 3A:
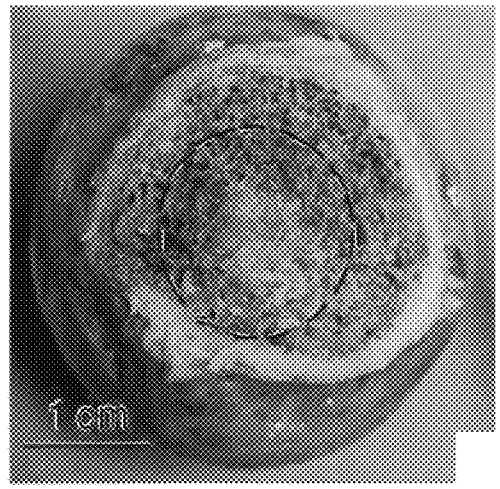
Figure 3B:
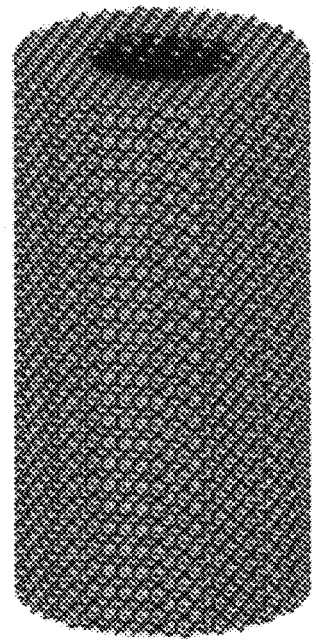
Figure 3E:
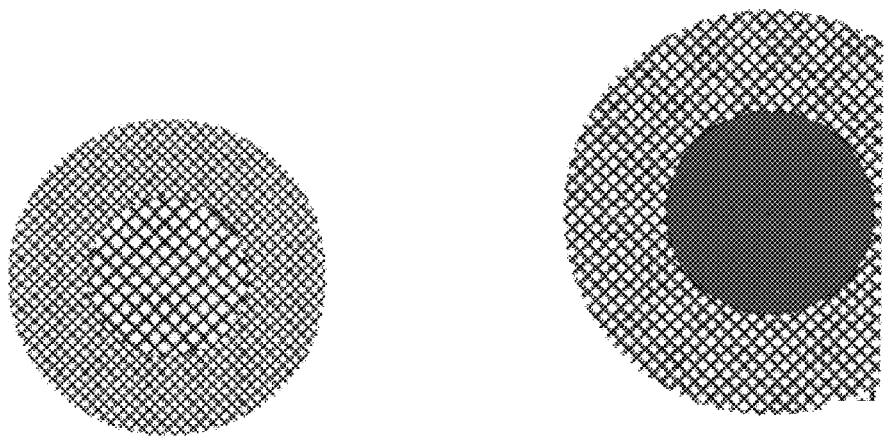
Figure 3E:
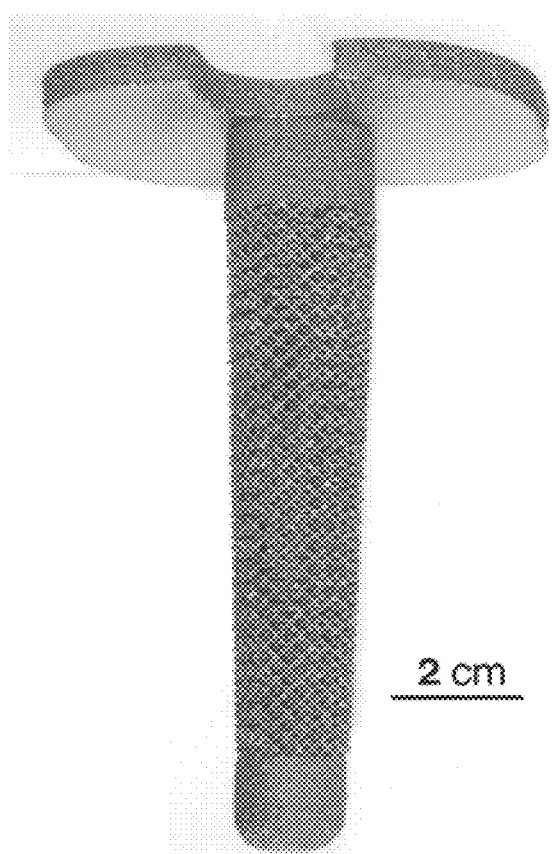

FIG. 2 shows examples of Ti-6Al-4V mesh components and component geometries (FIG. 2A-2C) along with a cranial section mesh replacement (FIG. 2C) built with the same software from a CAD system based on a cranial CT scan. The mesh density is roughly 1.8 g/cm$^3$, slightly less than cranial bone density. FIGS. 3A and 3B show some additional mesh system prototypes. In FIG. 3A is shown an upper femur cross-section view showing the outer (cortical) bone area and the central medullary (trabecular bone) area where the significant difference in porosity and graded density is apparent. FIGS. 3B and 3C shows a CAD mesh system for building a compatible 2-density intramedullary rod to be inserted within the dotted region in FIG. 3A. FIG. 3D shows a top view of a similar CAD system but having a solid core with aporous (cellular mesh) outer region. This CAD system was embedded in a build routine for an exaggerated tibial knee stem illustrated in FIG. 3E. The stem section is a tapered insert roughly twice the length of commercial knee replacement stems. The actual cellular mesh density for the prototype in FIG. 3E was ~1.4 g/cm$^3$.

FIGS. 1C, 2A, and 3B to 3E illustrate square mesh geometries viewed axially but these geometries present cube and hexagonal mesh arrays when viewed at 45° intervals along some reference system implicit in FIG. 2C. This is somewhat apparent on viewing FIGS. 3B and 3E. These cellular mesh geometries can of course be changed, and in stem or rod inserts the maximum stress distribution can be accommodated by optimized geometries built from lattice elements characteristic of the software. In addition, graded mesh geometries and cellular mesh arrays have been constructed which can provide for functional grading of stress or modulus within the bone section, and allowing for optimization of tissue ingrowth as well as prospects for intramedullary tissue and cell growth through the open cellular mesh arrays illustrated in FIGS. 3B and 3C for example. These and other features can be formed using the composition, methods and systems taught herein, e.g., those manufactured as shown in the example provided in FIG. 3E. The success of the fabricated reticulated mesh or mesh arrays, open cellular foams (both solid ligaments and hollow ligaments) and combinations, as well as monolithic combinations with solid materials, is dependent in most cases on the removal of excess or unmelted powder in the product or component interior.

Figure 4A:
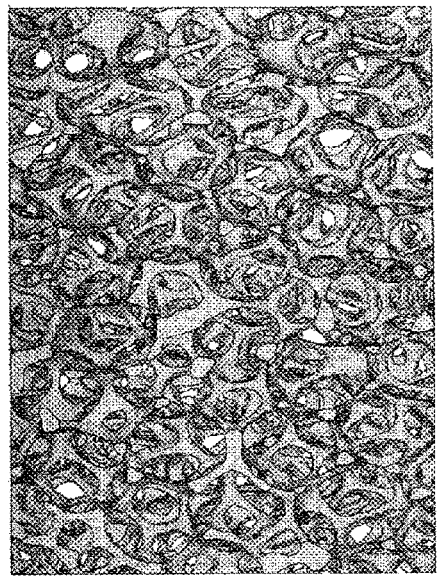
FIGS. 4A-4D shows CAD renderings of metal (aluminum alloy) cellular foam from micro-CT scan.
Figure 4B:
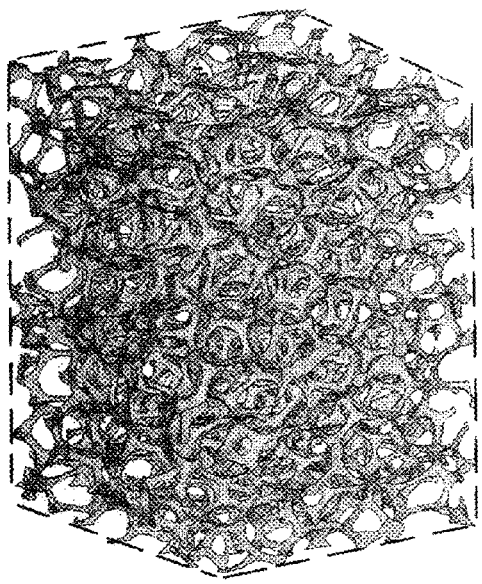
Figure 4C:
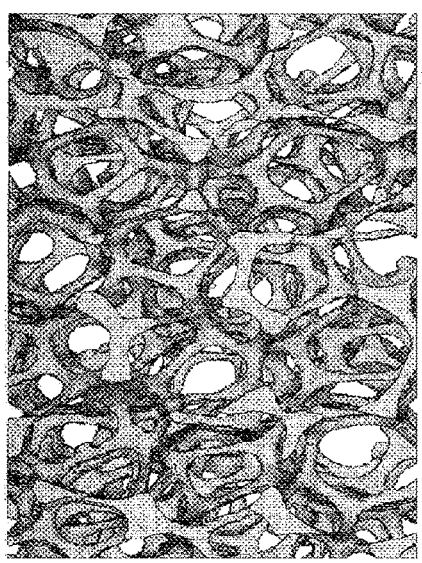
Figure 4D:
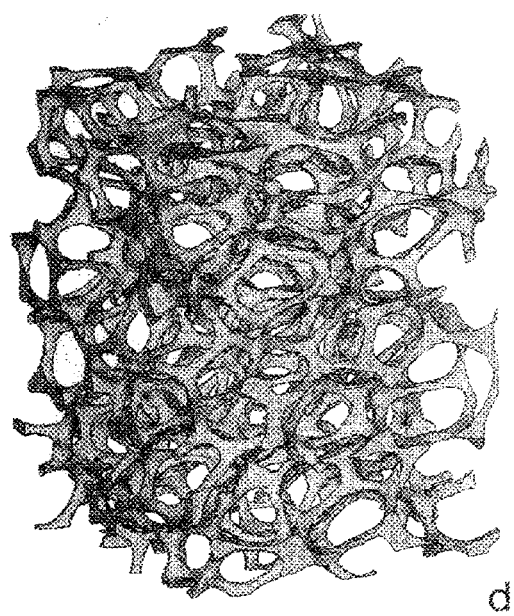
Figure 5A:
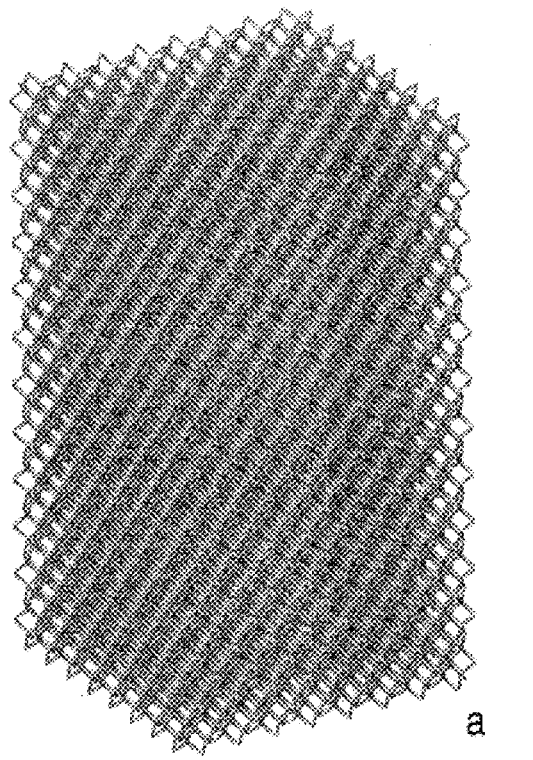
Figure 5B:
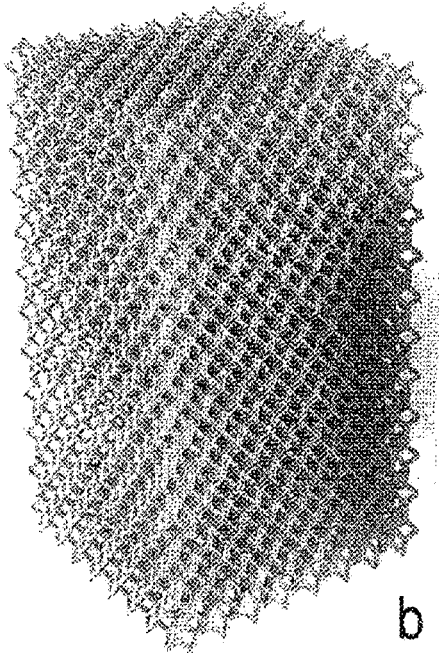
Figure 5C:
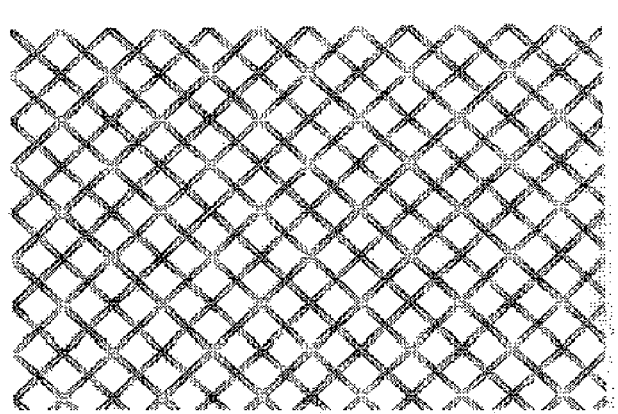
Figure 5C:
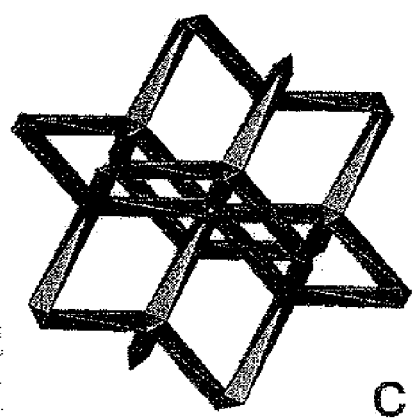

FIGS. 4A-4D shows CAD renderings of metal (aluminum alloy) cellular foam from micro-CT scan. (FIGS. 4A and 4B) 2× base foam or starting build unit, (FIG. 4B) 3× base foam, FIGS. 4C and 4D show 3D test blocks CAD element corresponding to FIGS. 4A and 4B respectively. Base foam porosity—6 PPI. Measured densities corresponding to FIGS. 4A and 4B are 0.83 g/cm$^3$ and 0.58 g/cm$^3$.

FIGS. 5A-5F show CAD model views and EBM fabricated prototypes utilizing the Materialize™ dode-thin software/CAD element.

Figure 6A:
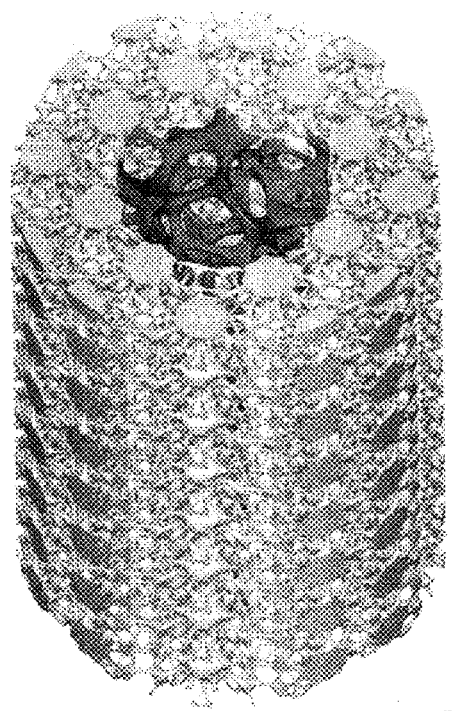
FIGS. 6A-6C show CAD models incorporating an inner foam element and an outer S3-bone element.
Figure 6B:
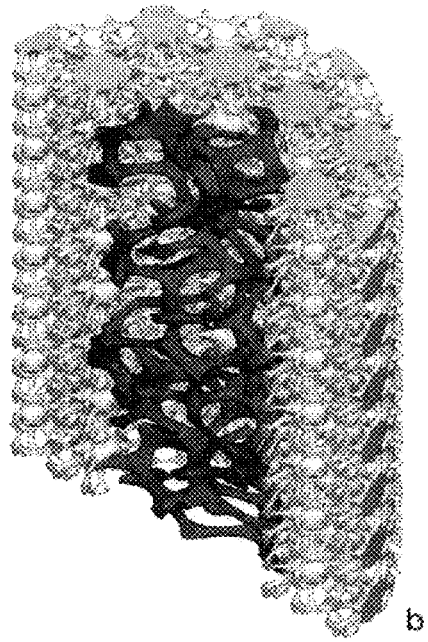
Figure 6C:
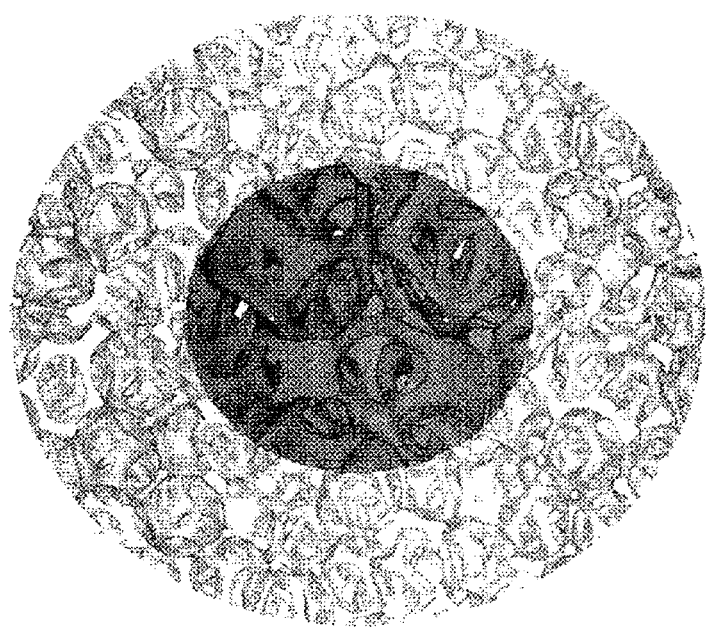
Figure 7A:
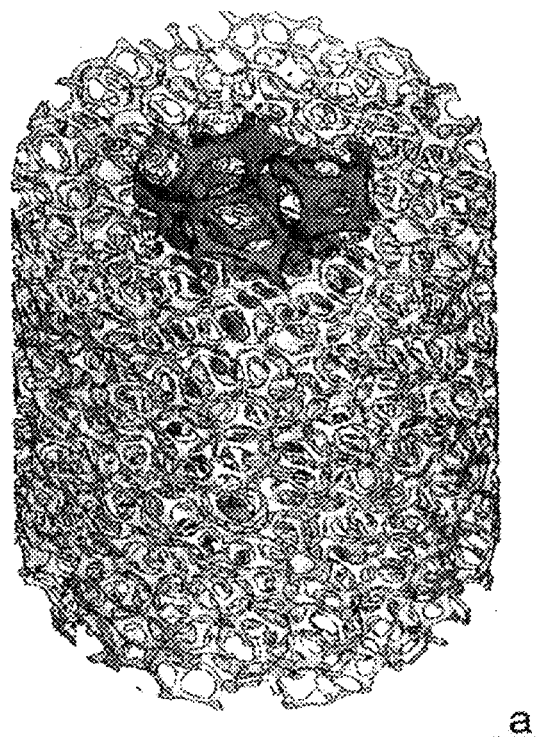
FIGS. 7A-7C show CAD models incorporating different density inner and outer foam elements as in FIG. 6.
Figure 7B:
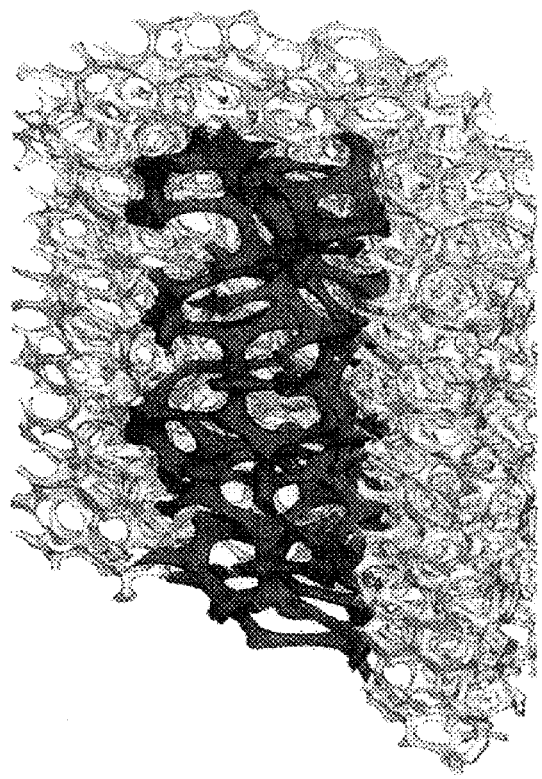
Figure 7C:
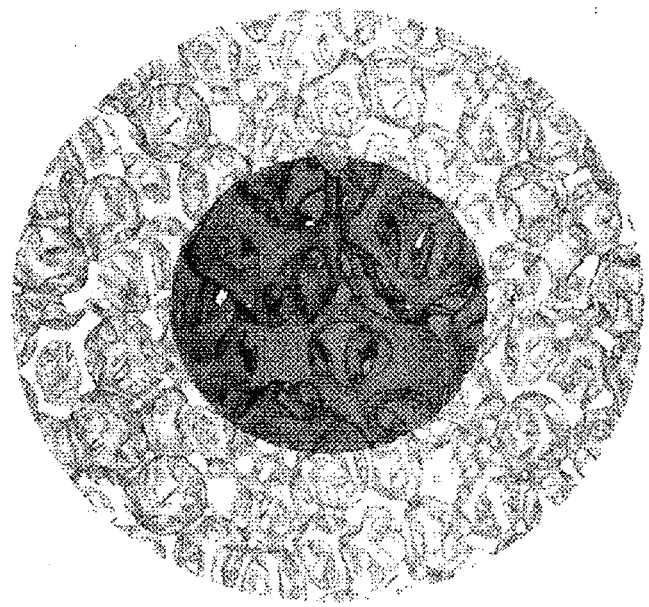

FIGS. 6A-6C show CAD models incorporating an inner foam element and an outer S3-bone element. FIGS. 6A-6C show 3D, 3D half-section, and end views, respectively. CAD models incorporating different density inner and outer foam elements as in FIG. 6 are shown in FIGS. 7A to 7C (3D, 3D half section, and end views, respectively). It can be seen that any combination of foams can be joined or functionally fabricated as a single, layer-manufactured monolithic product including: foam (open or closed cellular structure: solid or hollow cell ligaments)-to-foam, foam-to-mesh (or reticulated mesh arrays), mesh arrays-to-mesh-arrays, foam/foam/solid material, foam/mesh/solid material or any combination creating a contiguous, layer-manufactured-monolithic component or product.

Figure 8A:
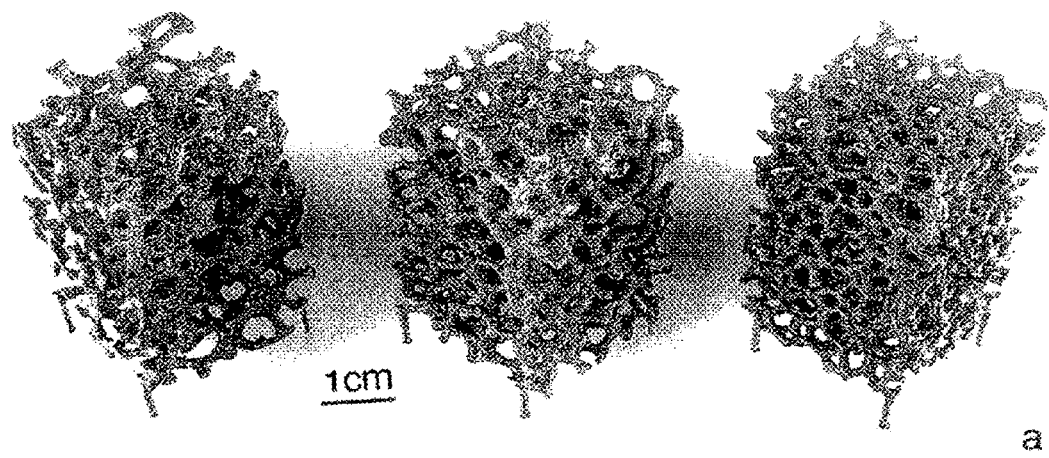
FIGS. 8A-8C show that open and closed cellular foams can be fabricated by electron and laser beam layer manufacturing.
Figure 8B:
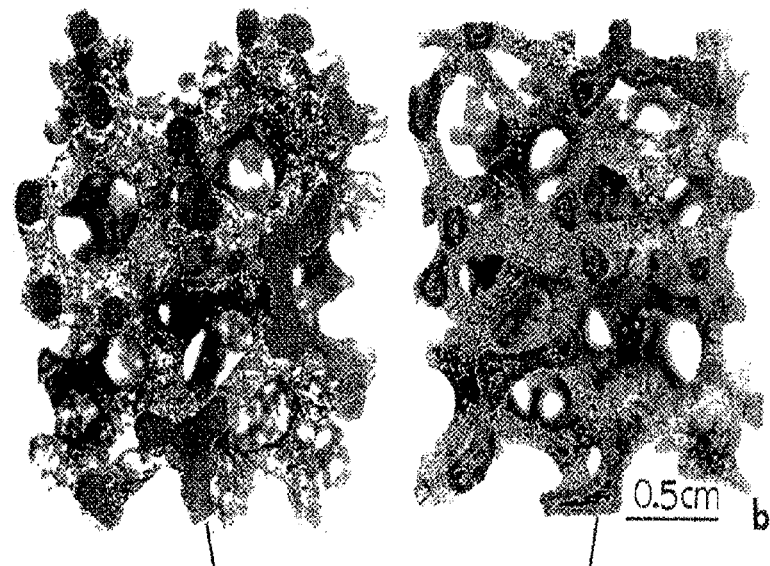
Figure 8C:
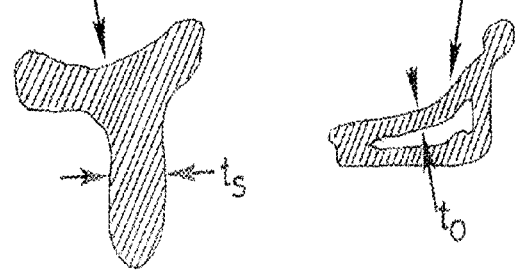

As illustrated in FIGS. 8A-8C, both open and closed cellular foams can be fabricated by electron and laser beam layer manufacturing. These foams are created from CT-scans of common aluminum foams or any other foam products which are easily fabricated from the melt, and embedded in a CAD model which can direct the layer building process. Foams can be created from virtually any powder material, including materials impossible to fabricate into foams by any other manufacturing process using electron or laser beams. These include, but are not limited to, titanium, titanium alloys (as shown for example in FIG. 2 for Ti-6Al-4V fabricated by electron beam melting), cobalt and nickel alloys, including nickel-based super alloys, etc.

In the instant invention the inventors have not only fabricated open cellular foams in Ti-6Al-4V, but these cellular foams are fabricated with solid cell ligaments and hollow or open cell ligaments, using appropriate CAD models. Control of the cell or ligament thickness or hollow cell-wall thickness allows for density and strength manipulation for the foam. Strength variations occur because of solidification or cooling rate variations which occur with different cell ligament or wall thickness.

CASE STUDY II—Solid and mesh Cobalt-base alloy prototypes by electron beam melting of Co-26Cr-6Mo-0.2C powder.

In addition to fabrications with the Ti-6Al-4V powder, the present inventors have fabricated solid geometries (with a density of 8.4 g/cm$^3$), as-fabricated and fabricated and annealed femoral (knee) prototypes, and reticulated mesh components (with a density of 1.5 g/cm$^3$) by additive manufacturing (AM) using electron beam melting (EBM) of Co-26Cr-6Mo-0.2C powder.

Cobalt-base alloys or cobalt-base superalloys (most commonly known as Deloro Stellite® alloys) have been used extensively in cast and hardfacing forms over the past two decades [17-19]. Typical applications have involved a variety of bearing materials or high temperature and high wear resistance applications such as valve seats in nuclear power plants, automobile engines, aerospace fuel nozzles and engine vanes and components, as well as biomedical implants [20-22]. Common Stellite® compositions include the standard Co-base alloy, Stellite 21 (with a nominal composition of 27% Cr, 5.5% Mo, 3% Fe, 2% Ni, 1% each Si and Mn, and 0.25% C; balance Co, in weight percent). A popular variance includes the Co-27Cr-5Mo-0.05C alloy or stoichiometric ranges encumbered under ASTM F75 standards: 27-30% Cr, 5-7% Mo, <0.35% C, <1% Si, Mn, <0.25 Fe, <0.5 Ni, balance Co in weight %, which apply to the preferred cobalt-base alloy for biomedical (implant) applications. While pure cobalt is characterized by an (hcp) low-temperature phase and an fcc, γ-phase at higher temperature, the addition of Cr improves the corrosion and oxidation resistance as well as the hardness, ductility, and wear resistance through carbide formation: Cr23 C6 (also Cr17Co4Mo2 C6), M6 C and M7 C3, depending upon the carbon content and kinetics. Molybdenum acts as a solid-solution strengthener by forming the intermetallic Co3 Mo (hcp phase) as well as improving the corrosion resistance of the alloy [20].

The ε (hcp)→γ (fcc) transformation in pure Co takes place at 430° C. (As) while the reversible γ→ε transformation occurs on cooling at 390° C. (Ms). However, upon alloying with Cr and other elements as noted, As is increased significantly. For example As is 970° C. for the Co-27Cr-5Mo-0.05C alloy [23]. The γ→ε transformation is also induced by plastic deformation or quenching from the temperature range of the stable γ-phase [24]. Cooling from the melt produces primarily γ (fcc) while rapid solidification can produce mixed phase systems as noted above, including carbides [17].

Traditional surgical implant Co-base alloys over the past several decades have been produced in cast or wrought forms [25,26] and heat treated to develop requisite properties under ASTM F75 or similar standards. These standards are characterized by residual hardness ranging from HRC 25-40, strength (UTS)/yield stress of 0.9 GPa/0.5 GPa and <1% to ~5% elongations for cast and wrought products respectively. Recent experimental production of Co—Cr—Mo alloy by laser powder microdeposition [27] has been shown to have microstructures similar to Co-based (Stellite®) hardfacing alloys deposited by arc welding and laser cladding [21] to develop abrasive wear features.

The present inventors have conducted extensive studies and evaluations of a number of Ti-6Al-4V prototype products fabricated by additive manufacturing (AM) using electron beam melting (EBM) [16,28-32]. These have included various simple, solid geometries as well as reticulated mesh arrays [31], open cellular foams [31,32], and complex, multifunctional components having varying densities and geometries for innovative applications in biomedical, aeronautical, and automotive areas [31-33]. EBM fabrication is a relatively new manufacturing concept involving solid freeform fabrication (SFF), which can create complex products from precursor powders by selectively melting individual powder layers using a CAD system to direct the electron beam. This layer building is particularly compatible with digital layer data such as that which characterizes CT-scans, and these allow for the development of CAD programs.

The fabrication of Co-26Cr-6Mo-0.2C (cobalt-base alloy) components by EBM is described herein. The components included several simple/solid (fully dense) geometries, specialized biomedical prototypes and reticulated mesh arrays. These components were examined by optical metallography, scanning electron microscopy (including energy-dispersive X-ray spectrometry (EDS)), transmission electron microscopy, and XRD. Structural and microstructural observations were composed and correlated with mechanical property measurements which included, where feasible, tensile testing, and microindentation hardness measurements. Fracture surface microstructures were examined using scanning electron microscopy.

Figure 9A:
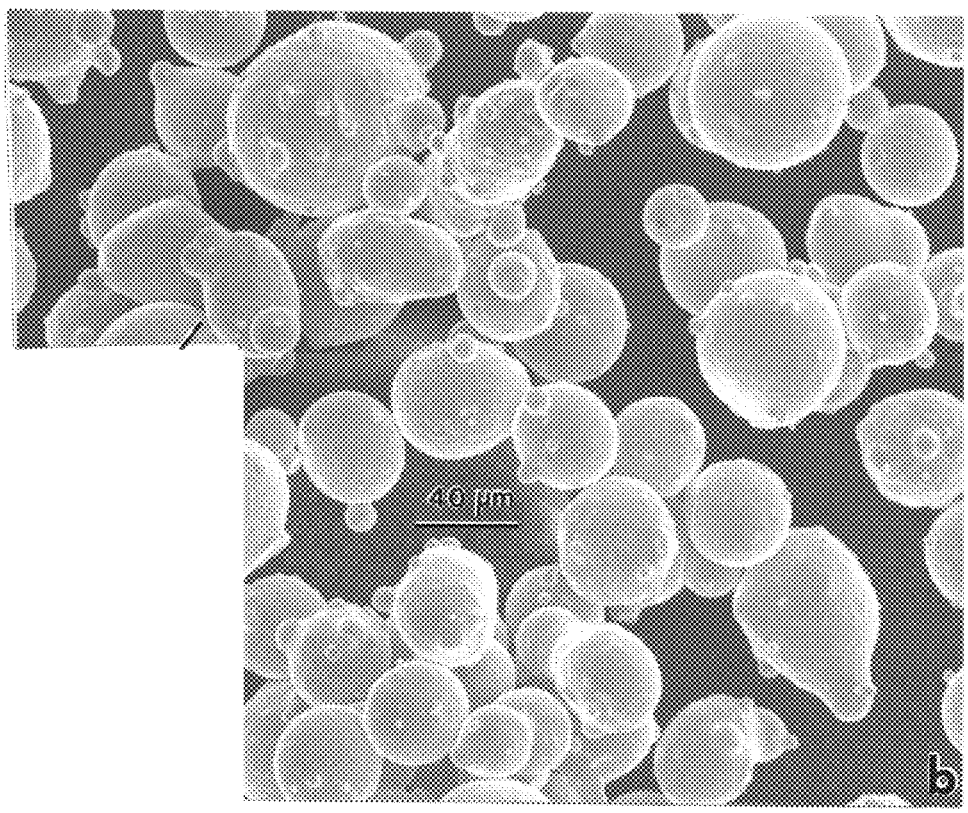
FIGS. 9A-9C show.
Figure 9B:
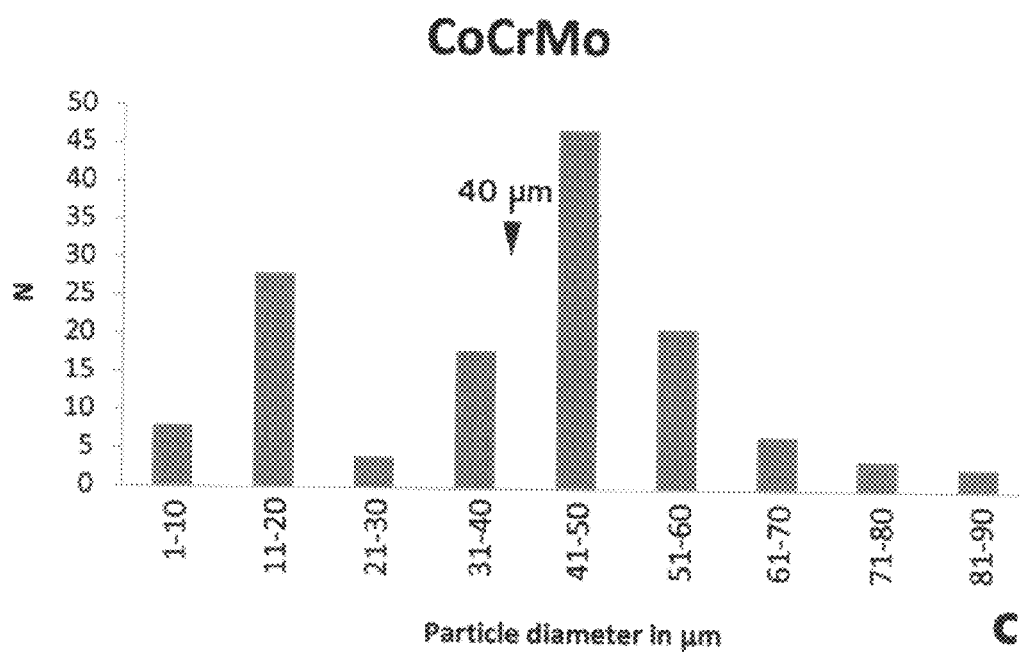
Figure 9C:
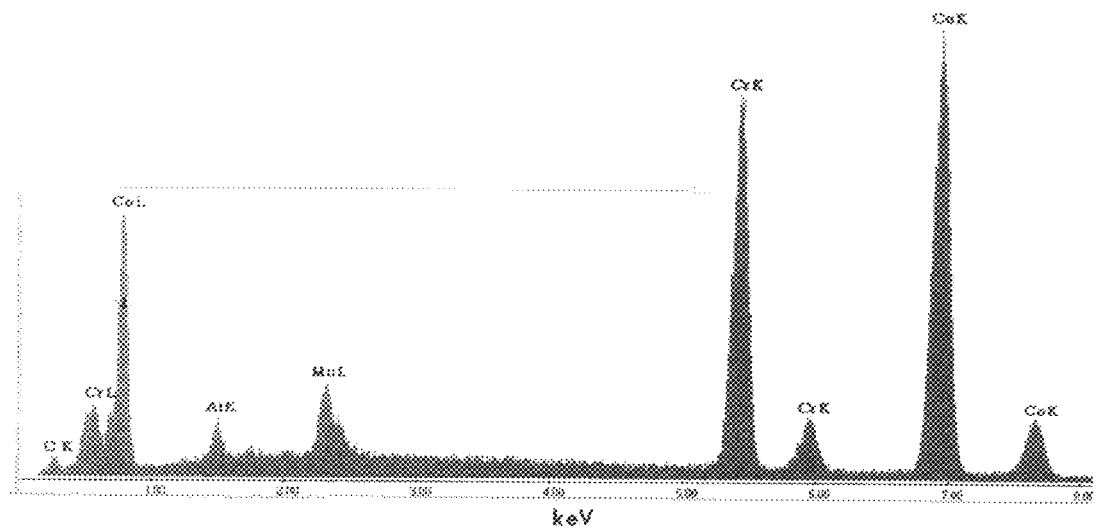

The Arcam A2 EBM system utilized for the fabrication of a number of component geometries from Co—Cr—Mo precursor powder has been previously described in FIG. 1A. Co—Cr—Mo powder (FIG. 9A) having a nominal composition shown in FIG. 9C and Table I was gravity fed from cassettes 108 onto a build table 114 where it was raked (r) into a layer thickness of ~100 µm. The nominal powder size (~40 µm) and size distribution (which illustrates a bimodal feature as a consequence of satellite particles attached to larger particles) are shown in FIG. 9B. Each newly raked powder layer is initially rastered by the electron beam at high beam current in alternating (X-Y), multiple passes to preheat the layer to ~830° C. The melt scan is rastered at $1-2 \times 10^3$ mm/s at a reduced beam current of ~10 mA. The melt scan is driven by a 3D-computer-aided design (CAD) program which melts only prescribed layer portions for the building component. The beam scan direction is alternated to 90° (perpendicular) every other layer build. The build chamber in the EBM system (FIG. 1A) has a nominal vacuum of $10^{-4}$ torr where a helium gas bleed at the build zone reduced the vacuum to $\sim 10^{-2}$ torr to facilitate build cooling and thermal stability.

TABLE I

Chemical composition for precursor Co—Cr—Mo Powder and EBM fabricated components.

| Material Component | Element (weight %) | | | | | | | | |
|---|---|---|---|---|---|---|---|---|---|
| | Cr | Mo | C | Fe | Ni | Si | N | $M_n$ | Co |
| ASTM F75* | 27-30 | 5-7 | <0.35 | <0.75 | <0.50 | <1.0 | <0.25 | <1.0 | Bal. |
| Powder† | 29 | 6 | 0.22 | — | 0.25 | 0.7 | 0.15 | 0.5 | Bal. |
| As-Fab. Knee†† | 26 | 4.4 | — | — | — | — | — | 1 | Bal. |
| Mesh†† | 28 | 5.2 | — | — | — | — | — | — | Bal. |

*ASTM F75 Standard chemical composition/composition ranges.
†Chemical analysis by mass spectrometry
††Chemical analysis by energy-dispersive X-ray spectrometry (EDS)

A range of EBM built Co—Cr—Mo component geometries were fabricated for analysis in the present invention. These included simple, fully dense (8.4 g/cm³) cylindrical and orthogonal (block) structures (FIG. 10A) femoral, knee implant components, and orthogonal, open-cellular mesh components similar to those previously described hereinabove in the EBM fabrication of Ti-6Al-4V mesh components [31-33]. The implant and mesh structures were created using selective space structures (3S) software, a product of Fruth Innovative Technologien GmbH (FIT), Germany (www.pro-fit.de). The specific mesh (3S) structure generator or unit cell was 3S-diamond. These structure generators build CAD models as described previously [31].

An as-fabricated, femoral knee component was annealed and rough-polished. Annealing (heat treatment) followed ASTM F75 CoCr Alloy standard and consisted of initial, hot isostatic pressing (HIP) at ~1200° C. for 4 h in Ar at $10^3$ bar, followed by a quench from a homogenizing treatment at 1220° C. for 4 h in Ar, at 75° C./min. This homogenizing temperature was ~0.8 TM; where TM (the melting temperature) is ~1430° C. This homogenizing temperature allowed for significant grain growth and carbide dissolution.

Microstructural and Microchemical Characterization: Microstructures for the various EBM-built components were observed and examined initially by optical metallography (OM) and X-ray diffraction/diffractometry (XRD), followed by SEM and TEM; both utilizing energy-dispersive (X-ray) spectrometry (EDS). TEM analysis also utilized selected-area electron diffraction (SAED) coupled with, and facilitating, dark-field imaging of selected microstructures. The OM was performed using a digital imaging Reichert MEF4 A/M system after specimens/sample coupons were variously cut from each component, polished, and etched. The precursor Co—Cr—Mo powder illustrated in FIG. 9A was also mounted, polished, and etched to reveal the initial microstructures. Etching protocols varied for specific samples. The cylindrical and orthogonal, rectangular components were etched with a solution consisting of 6:1 HCl:$H_2O_2$ (3%) for 16 h at room temperature, while the as-fabricated and annealed knee and mesh components were etched for 1-2 min. In contrast, the annealed and polished knee component along with the mounted and polished precursor powder were etched with a solution consisting of 100 mL $H_2O$, 50 mL HCl, 10 mL $HNO_3$, and 10 g $FeCl_2$ for short times (ranging, from 1-2 min.). The as-fabricated knee component was etched in a 12:1 HCl:$H_2O_2$ (3%) solution for 16 h.

XRD spectra were obtained for the precursor powder (FIG. 9A) and from representative samples extracted from several of the EBM fabricated components. The XRD system was a Bracker AXS-D8 Discover system using a Cu target.

SEM analysis utilized a Hitachi S-4800 field-emission (FE)-SEM fitted with an EDAX EDS system, and operated primarily at 20 kV accelerating potential in the secondary electron emission mode. An example of these images is shown in FIG. 9A. The TEM analyses were performed in either a Hitachi H-8000 analytical TEM fitted with a goniometer-tilt stage and operated at 200 kV, or a Hitachi H-9500 high-resolution TEM fitted with a goniometer-tilt stage, an EDAX-EDS system, and operated at 300 kV accelerating potential. Samples were prepared for TEM analysis by cutting and carefully grinding coupons from the cylindrical and orthogonal, rectangular block components along with the as-fabricated knee component and the annealed and polished knee component. These coupons were ground and polished to a thickness of ~200 µm and 3 mm discs punched from these samples. The discs were mechanically dimpled and electropolished in a Tenupol-5, dual jet unit at temperatures ranging from 30-40° C. using an electropolishing solution consisting of 15% perchloric acid and 85% acetic acid, at 20V and 3-30 mA.

Figure 10A:
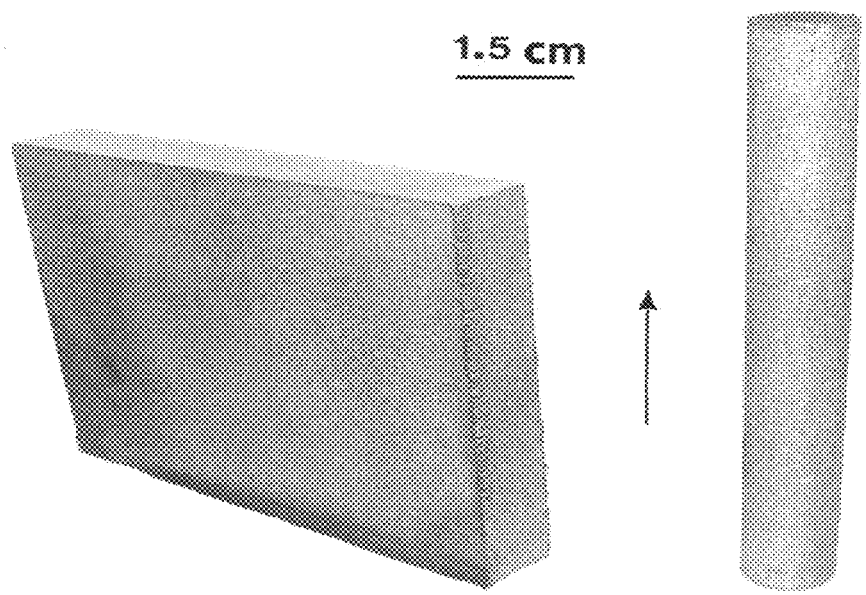
FIG. 10A-10C shows.
Figure 10B:
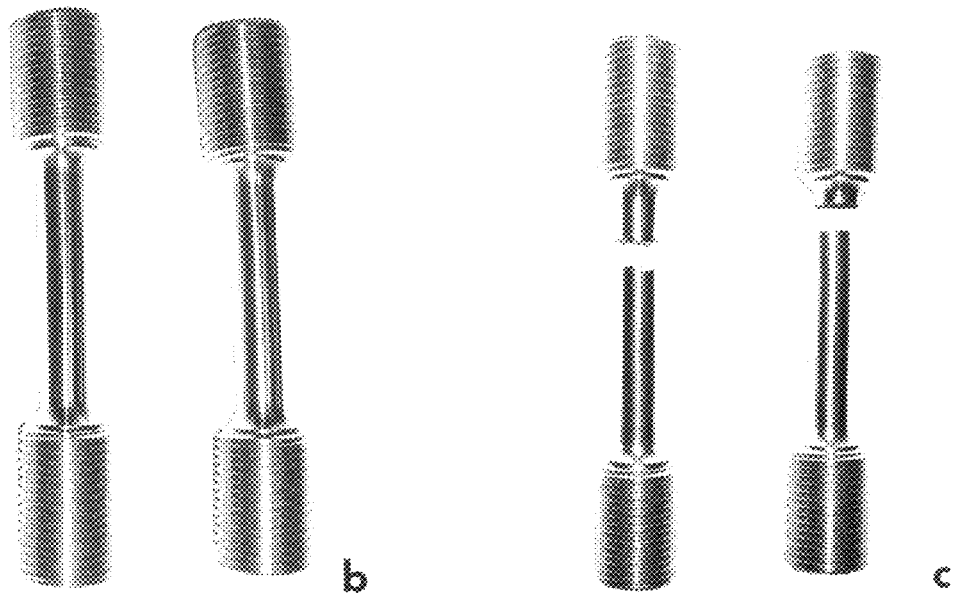

Mechanical Testing: Tensile specimens were machined from cylindrical build components, as illustrated in FIGS. 10A and 10B, and tested in an Instron 500 R tensile machine at a strain rate of $3 \times 10^{-3} s^{-1}$, at room temperature (~20° C.). Fracture surfaces for failed tensile specimens (FIG. 10C) were also examined in the FE-SEM.

Microindentation hardness and macroindentation hardness measurements were made using a Vickers hardness (HV) indenter (25-100 gf (0.25-1N) load at ~10 s load time) in a Shimadzu HMV-2000 system, and a Rockwell C-scale hardness (HRC) tester (1.5 kN load), respectively. Microindentation (HV) measurements on mounted, polished, and etched mesh samples utilized the lightest load (25 gf: 0.25N). All microindentation (HV) and macroindentation (HRC) measurements were averaged for a minimum of 10 indentations.

Figure 11A:
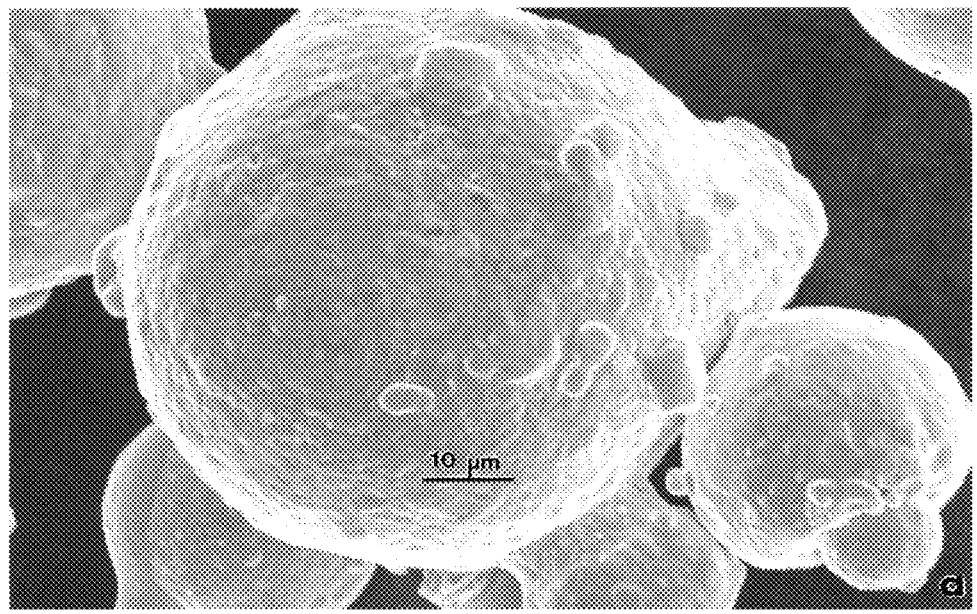
FIG. 11A is an enlarged SEM view of precursor Co—Cr—Mo powder in FIG. 9A.
Figure 11B:
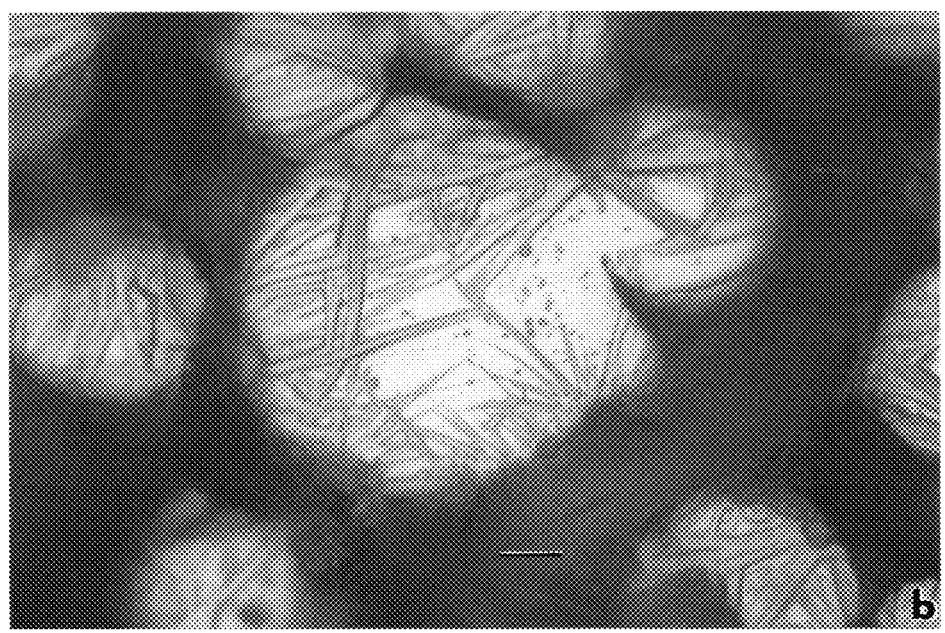
FIG. 11B shows mounted polished, and etched powder sections observed by optical metallography.
Figure 12:
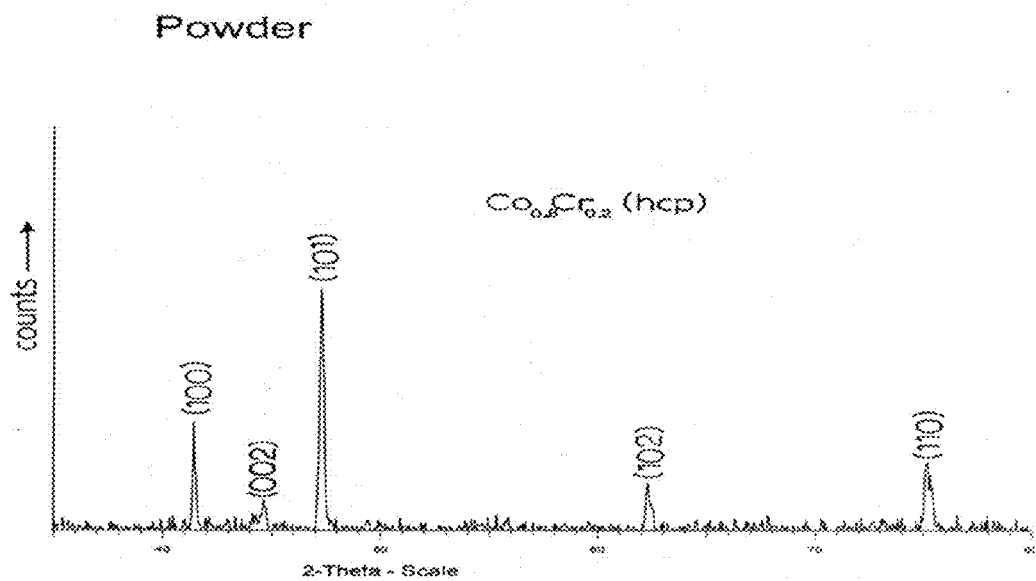
FIG. 12 is the XRD $Co_{0.8}Cr_{0.2}$ (hcp) spectrum for precursor powder in FIG. 9A. Indexed (hkl) diffracting planes are indicated.

Powder Characterization: FIG. 11A illustrates a magnified SEM view for the Co—Cr—Mo atomized, precursor powder shown in FIG. 9B. Correspondingly, FIG. 11B shows a section of powder placed in mounting material which was ground, polished, and etched to reveal a unique solidification microstructure. FIG. 12 illustrates the characteristic XRD spectrum for the Co—Cr—Mo powder in FIG. 9A to represent $Co_{0.8}Cr_{0.2}$ hcp/hexagonal crystal structure with a P63/mmc space group, and lattice parameters a=2.52 Å; c=4.06 Å. There was no evidence of carbides or intermetallic ordered compounds such as $Co_3Mo$ (hcp) as might be expected for incipient melting or slower solidification processes [34]. The precursor Co—Cr—Mo powder microindentation hardness measured on polished and etched sections similar to FIG. 11B averaged 6.3 GPa (630 HV) (Table II).

Figure 13:
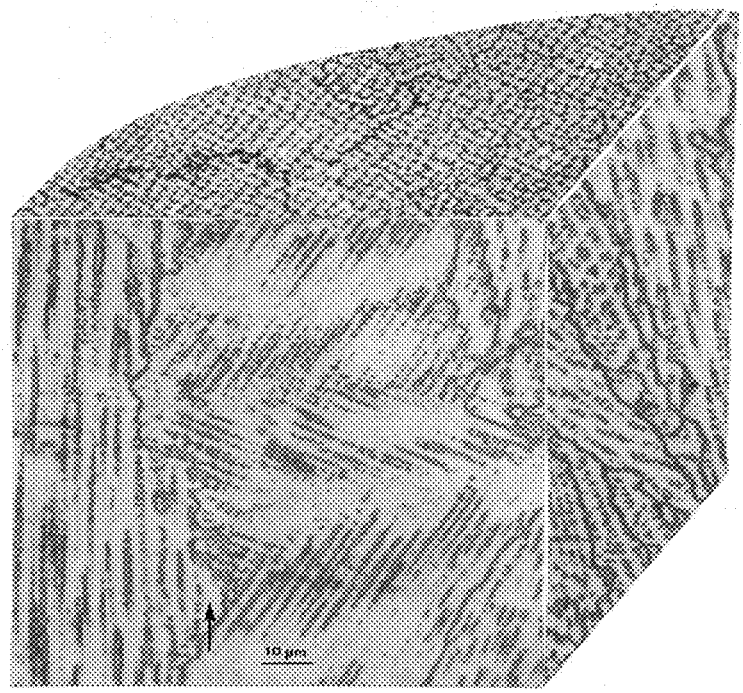
FIG. 13 is a 3-D optical metallography composite/section view for a mounted and etched cylindrical component as in FIG. 10A. Arrow indicates the EBM build direction in the vertical plane. Note orthogonal carbide arrays in the horizontal plane and connected carbide columns in the vertical plane (parallel to the build direction)
Figure 14:
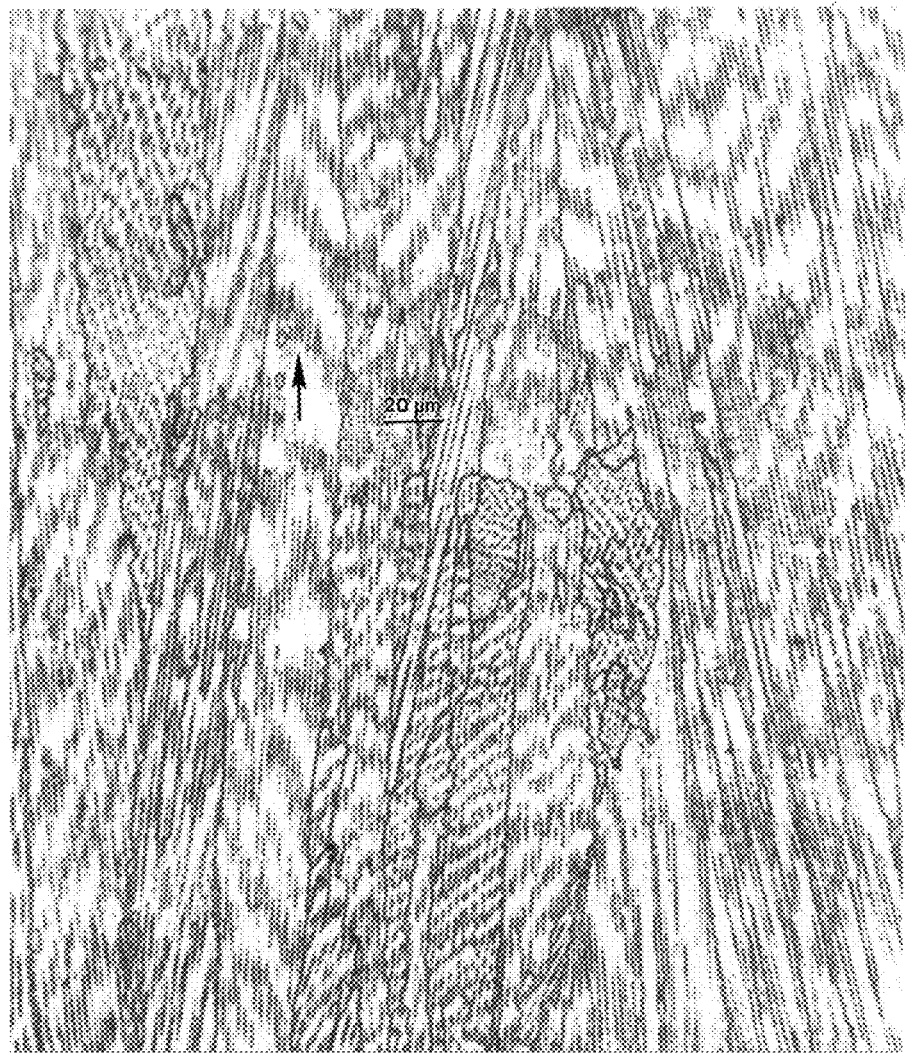
FIG. 14 is the cylindrical component vertical plane optical metallographic view showing complex carbide columns and related carbide arrays in the build direction (arrow)
Figure 15A:
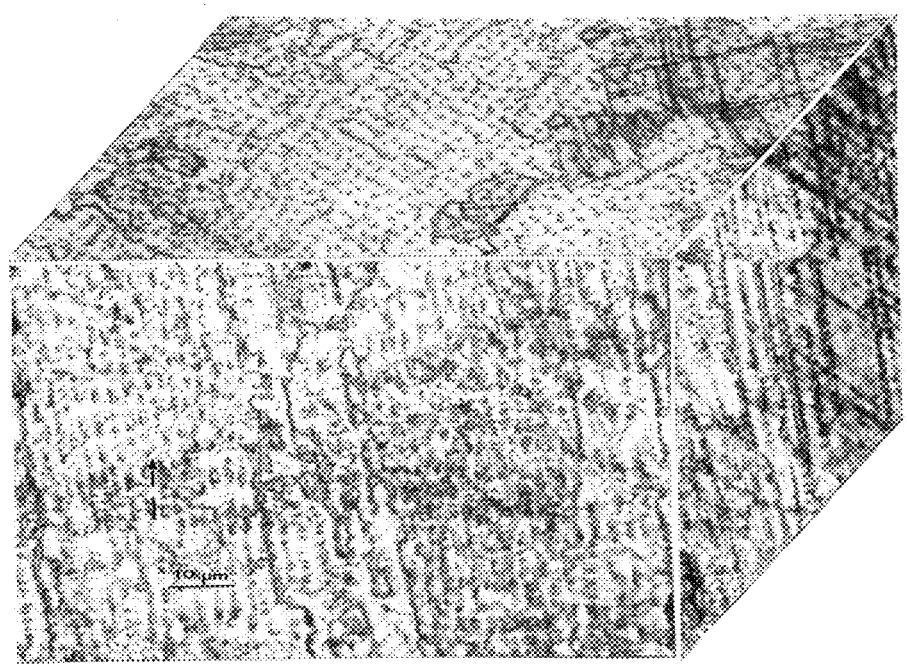
FIG. 15A is a 3-D optical metallography composite/section view for a mounted and etched rectangular block specimen cut from the EBM built component shown in FIG. 10A. The arrow to the left illustrates the build direction in the vertical plane.
Figure 15B:
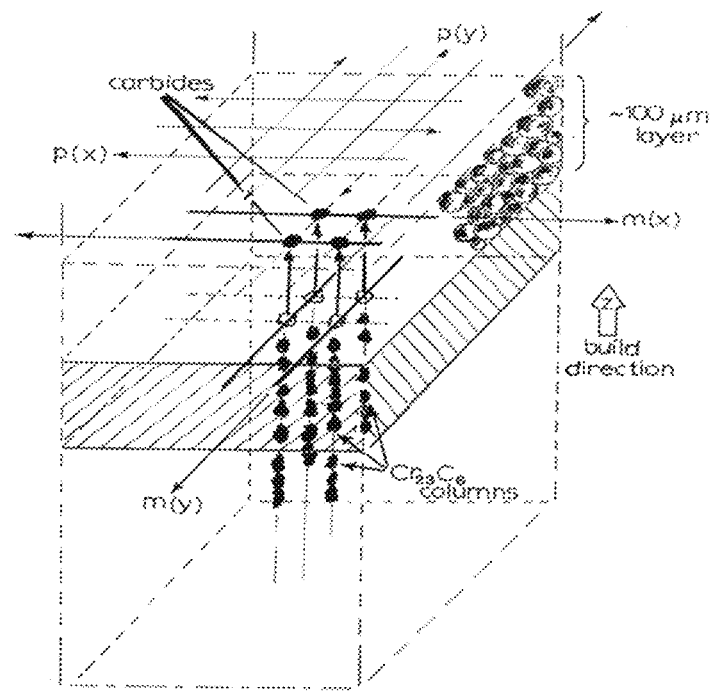
FIG. 15B is a schematic view of carbide precipitate pattern formation in FIG. 13 and FIG. 7(a) above. Note beam scan direction reverses each succeeding layer. P(x) and P(y) indicate preheat scans while m(x) and m(y) denote melt scans in successive layer building.

Characterization of As-Fabricated, Fully Dense Cylinders and Blocks: In contrast to the initial powder solidification microstructure shown in FIG. 11B, the EBM fabricated cylindrical and rectangular block components (FIG. 10A) where characterized by unique arrays of carbide microstructures illustrated typically in the optical metallographic images and image compositions shown in FIGS. 13-15. In FIGS. 13-15, the EBM build direction is indicated by the arrows. In FIGS. 13 and 15A regular carbide arrays representing precipitation in small domains created by the cross-scanning of the electron beam during preheating and in successive layer building, with dimensions of ~2 μm, are observed in the horizontal (or build) plane while similarly spaced columns of carbides are shown extending along the build direction (arrows), along with other regular and irregular columnar carbide features observed in the vertical planes parallel to the build direction (arrows). These unique microstructural features are highlighted in the vertical plane metallographic view shown for the cylindrical component in FIG. 14 which provides the appearance of zig-zag-like carbide features along with columnar-like grains and regular precipitate patterns, with dimensions similar to those shown in the horizontal plane views in FIGS. 13 and 15A (and having dimensions of ~2 μm). It can be noted in FIGS. 13-15A that the grain boundaries are also concentrated with carbides and are difficult in some cases to distinguish. Their sizes range from ~10 m to ~50 m, and more prominent as columnar grains in FIG. 14. The zig-zag-like carbide patterns arise by systematic beam scan shifts either in the preheat scans or in successive melt scans. FIG. 15B illustrates these carbide precipitation features schematically.

The arrays of carbides shown in FIGS. 13, 14, and 15A represent a controlled microstructural architecture which results from electron beam parameters, scan rates, and scan geometries which may be altered to produce a range of microstructural architectures resulting in predictable property and performance characteristics as a consequence of the architectural geometry and size scale. In addition, functionally graded microstructural architectures and associated property variations can also be achieved by electron beam build variations.

Figure 16:
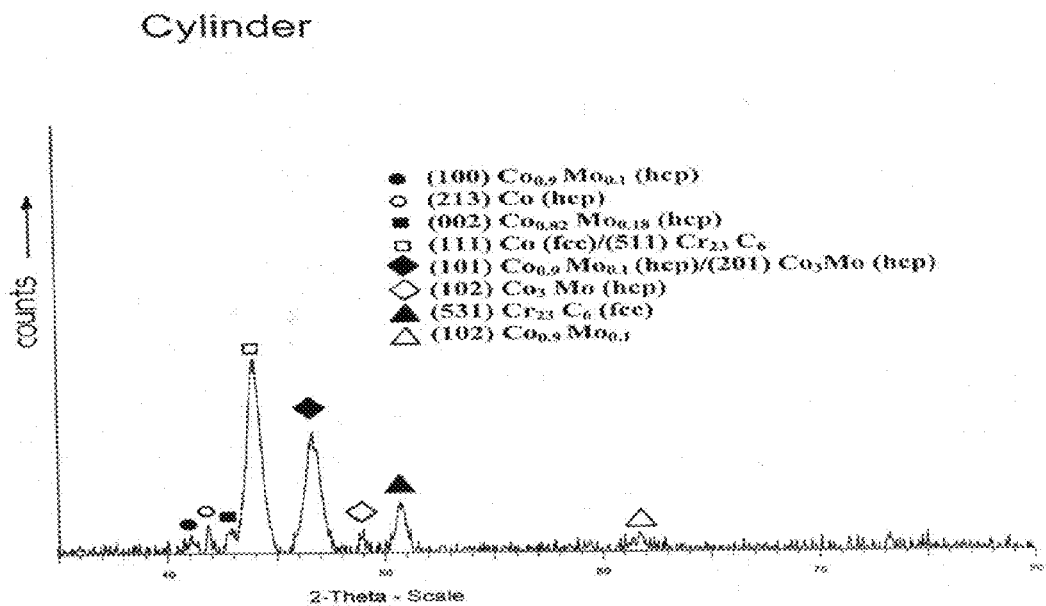
FIG. 16 is the XRD pattern corresponding to the horizontal plane view for the cylindrical component shown in FIG. 13. Indexed peaks are noted by keys.

FIG. 16 illustrates the corresponding XRD spectrum for a horizontal section cut from the cylindrical specimen represented by FIG. 13. In contrast to the powder XRD pattern (spectrum) shown in FIG. 12, FIG. 16 shows a variety of crystallographic and compositional phase mixtures, mostly hcp with a Co or CoCr fcc matrix. The only major carbide represented is $M_{23}C_6$ or $Cr_{23}C_6$ (fcc: a=10.66 Å); where M can also be $Cr_{17}Co_4Mo_2$ [17,19]. Note the overlap of (511) $Cr_{23}C_6$ with the (111) Co (fcc: a=3.55 Å) peak as well as the CoMo component overlap at 2θ=46.5°. A small ε-Co (hcp: a=2.51 Å, c=4.08 Å) peak occurs at 2θ=41.8°, and this hcp structure space group (P63/mmc) also characterized the other hexagonal components shown in FIG. 16: $Co_{0.9}Mo_{0.1}$ (a=2.52 Å, c=4.11 Å); $Co_{0.80}Mo_{0.18}$(a=2.60 Å, c=4.21 Å); CoMo (a—5.12 Å, c=4.11 Å).

TABLE II

Mechanical Properties for EBM Fabricated Co—Cr—Mo Components.

| COMPONENT | HARDNESS | | TENSILE† | | |
| --- | --- | --- | --- | --- | --- |
| | HV* (GPa) | HRC** | YIELD STRESS (GPa)†*† | UTS (GPa) | Elongation (%) |
| Precursor Powder | 6.3 | — | — | — | — |
| Solid Block | 4.4*† | 44/46†† | — | — | — |
| Solid Cylinder | 4.6*† | 47/48†† | 0.51 | 1.45 | 3.6 |
| As-Fabricated Knee (femoral) | 5.9 | 46 | — | — | — |
| Annealed/Polished Knee (femoral) | 4.7 | 40 | — | — | — |
| Mesh Array | 6.8/5.6†† | — | — | — | — |

*Vickers Microindentation hardness (VHN or HV): 1 VHN = 0.01 GPa.
**Rockwell C-scale hardness
*†Horizontal Plane
†Average for 2 tests
††Horizontal Plane Hardness/Vertical Plane Hardness
†*†0.2% engineering offset yield stress.

Microindentation hardness (HV) in the horizontal plane for the rectangular block sample (FIG. 15A) and the cylindrical sample (FIG. 13) averaged 4.4 and 4.6 GPa respectively (Table II). Corresponding Rockwell C-scale (HRC) measurements were also made in both the horizontal and vertical planes for the block (FIGS. 15A and 15B) and cylindrical (FIG. 13) samples as shown in Table II. These values are consistent with the nearly 0.1:1 conversion for HV: HRC values (Table II). The microindentation hardness values for the EBM fabricated cylindrical and rectangular block components are nearly 30% softer than the precursor Co—Cr—Mo powder in spite of the high carbide density or fraction, which averages ~0.2 to 0.3; and is similar to cast ASTM F75 Co—Cr—Mo alloy which is also dominated by $M_{23}C_6$ carbides [35]. The measured hardnesses are also consistent with Stellite® alloys which range from HV 4.1 to 5.5 GPa, and HRC 42-53.

Figure 17:
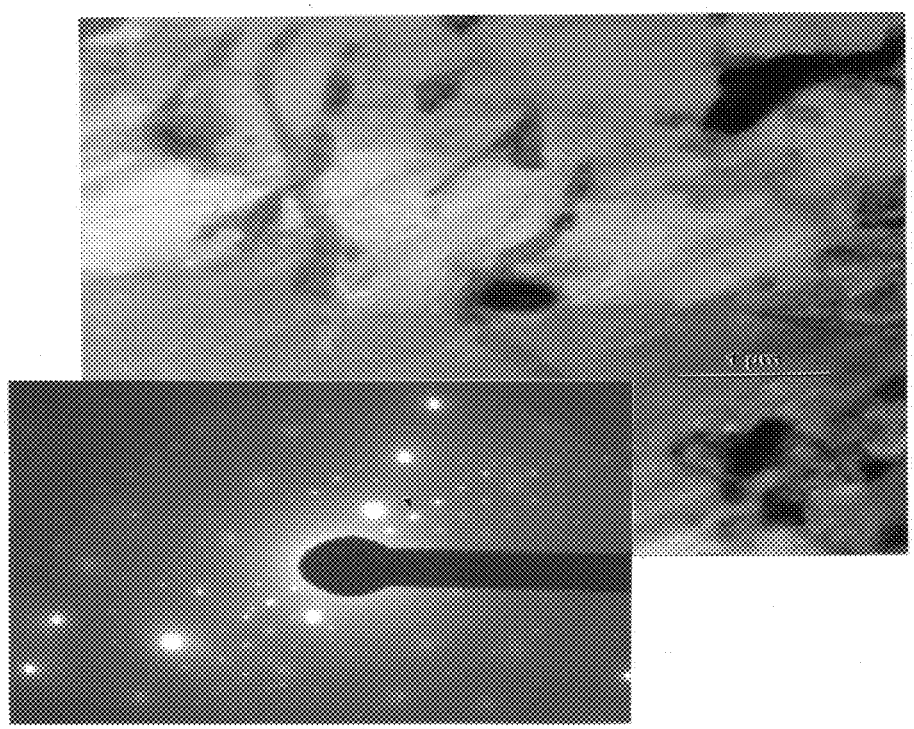
FIG. 17 is a TEM bright-field image showing horizontal plane thin section microstructure for a cylindrical component as shown in FIG. 13. Prominent microstructure features include Cr23C6 precipitates, dislocations and stacking faults. The SAED pattern insert shows fcc Co (matrix) diffraction spots and (100) fcc Cr23C6 diffraction spots (arrow)
Figure 18A:
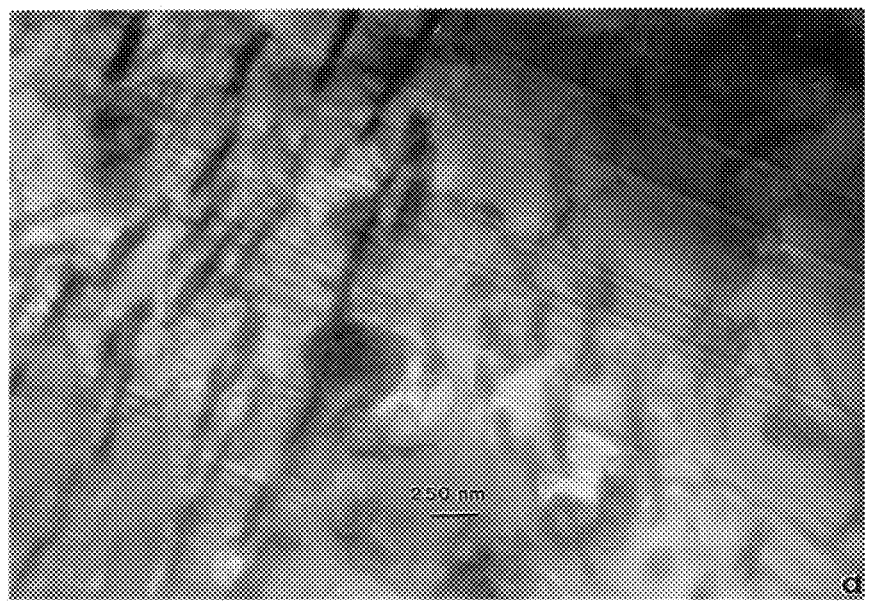
FIGS. 18A and 18B are TEM bright field image examples in the horizontal plane for the block component (FIG. 15A) showing.
Figure 18B:
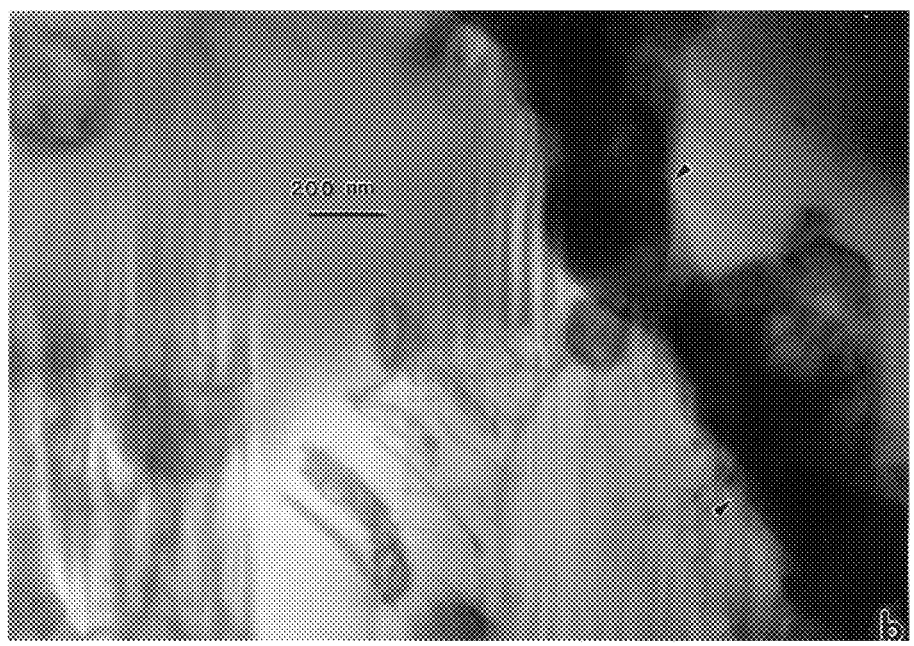

FIGS. 17 and 18 show bright-field TEM images for horizontal plane specimens from the cylindrical and rectangular block components, respectively. FIG. 17 shows carbide ($M_{23}C_6$) precipitates along with their corresponding and superimposed selected-area electron diffraction pattern in the SAED pattern insert. These images also show a high dislocation density and numerous stacking faults which attest to the fcc Co structure. Similar features are noted in FIGS. 18A and 18B for a horizontal section from the rectangular block component (FIG. 10A). Especially prominent in both FIGS. 18A and 18B is the relatively high stacking fault density, with numerous overlapping faults, which are characteristic of the very low stacking fault free energy (~15 mJ/m$^2$) for fcc Co [3]. FIG. 18B shows dense Cr23C6 precipitates within or associated with a grain boundary marked by small arrows. It can be noted in FIGS. 17 and 18 that the $Cr_{23}C_6$ carbides exhibit a variety of irregular microstructures.

Figure 19A:
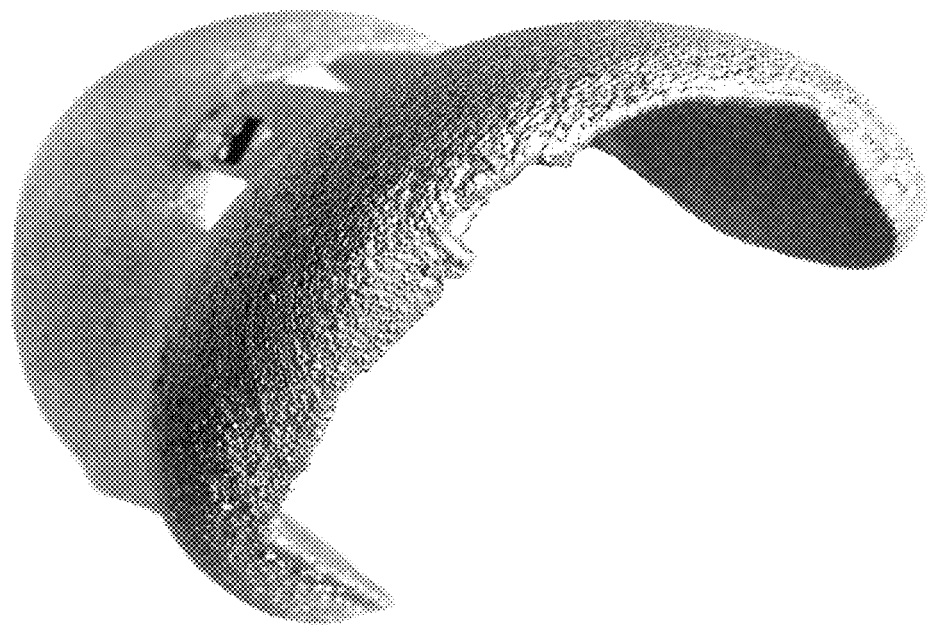
FIGS. 19A and 19B show as-fabricated (EBM) femoral (knee) prototype.
Figure 19B:
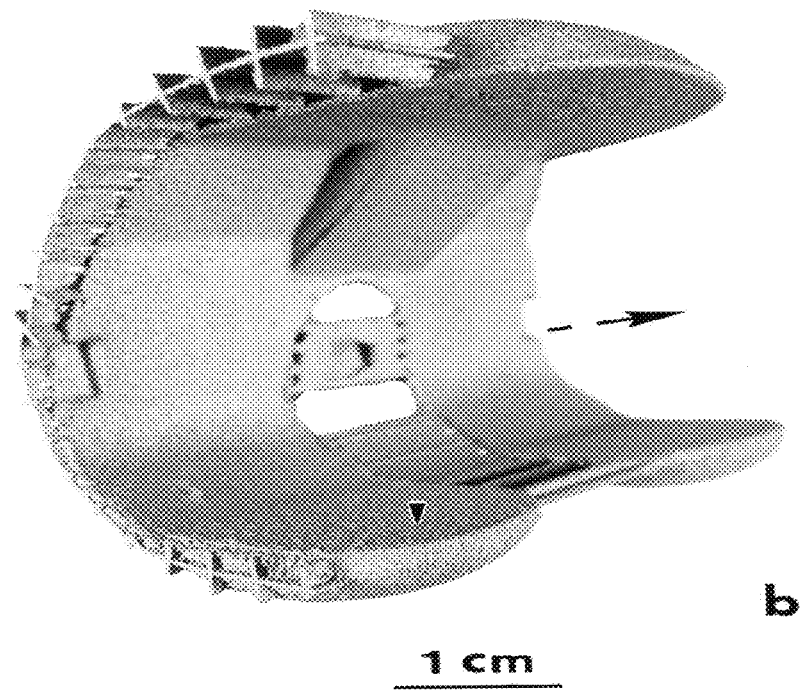
Figure 19C:
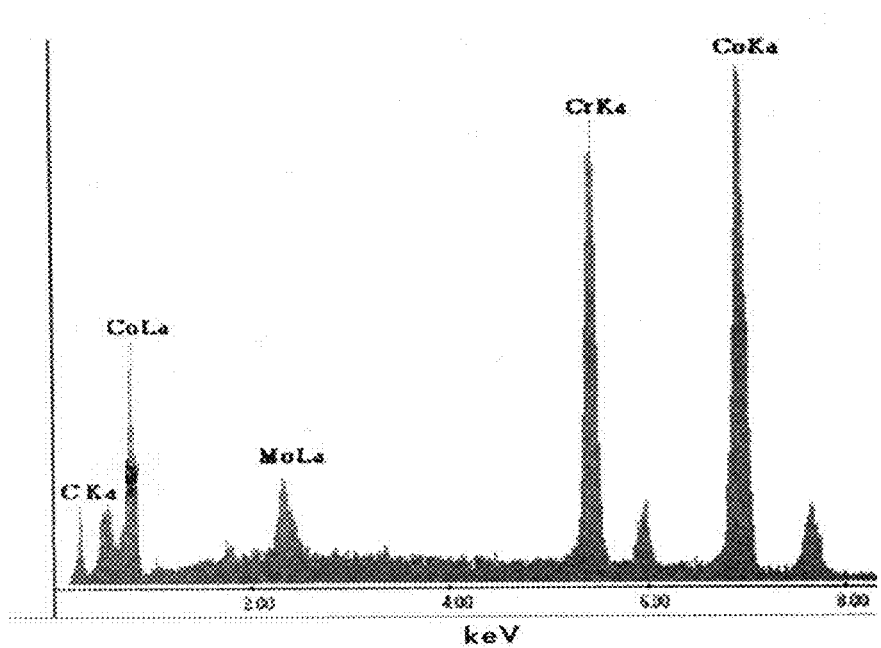
(FIG. 19C) shows the corresponding EDS spectrum for the section cut at small arrow in FIG. 19B and observed in the SEM.
Figure 20A:
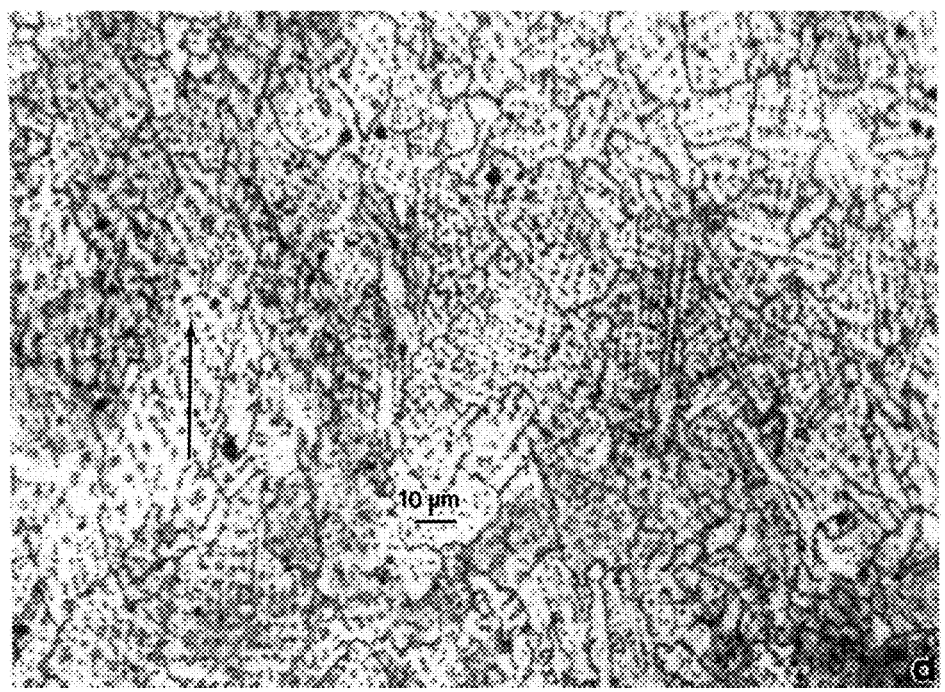
FIGS. 20A and 20B show optical metallography views for the cut section for the as-fabricated femoral (knee) component in FIG. 19B.
Figure 20B:
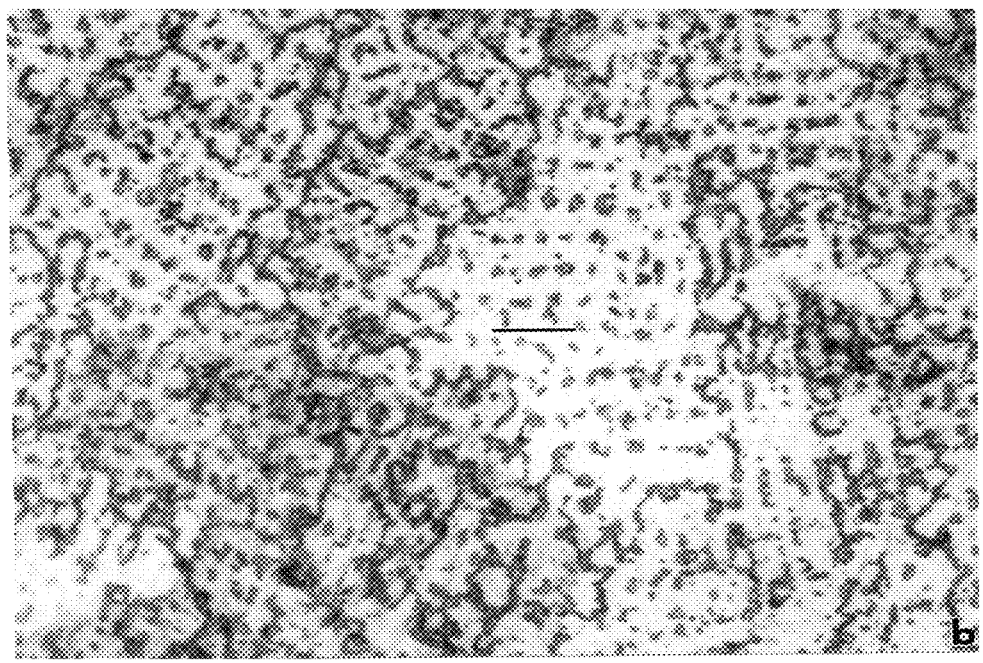
Figure 21A:
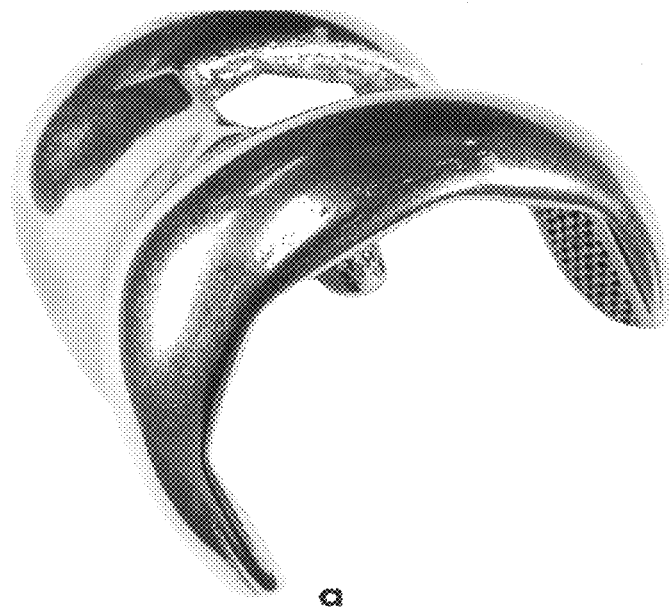
FIGS. 21A and 21B show annealed and polished femoral (knee) prototype built with porous mesh features for bone tissue ingrowth at femoral attachment shown in corresponding views. In 21B the larger arrow indicates the build direction as in FIG. 19B while the smaller arrow to the right indicates the sectioning of the component for examination, (FIG. 21C) shows a commercially implanted Co—Cr—Mo femoral (knee) component (arrow) and a Ti-6Al-4V tibial (knee) component (at t)
Figure 21B:
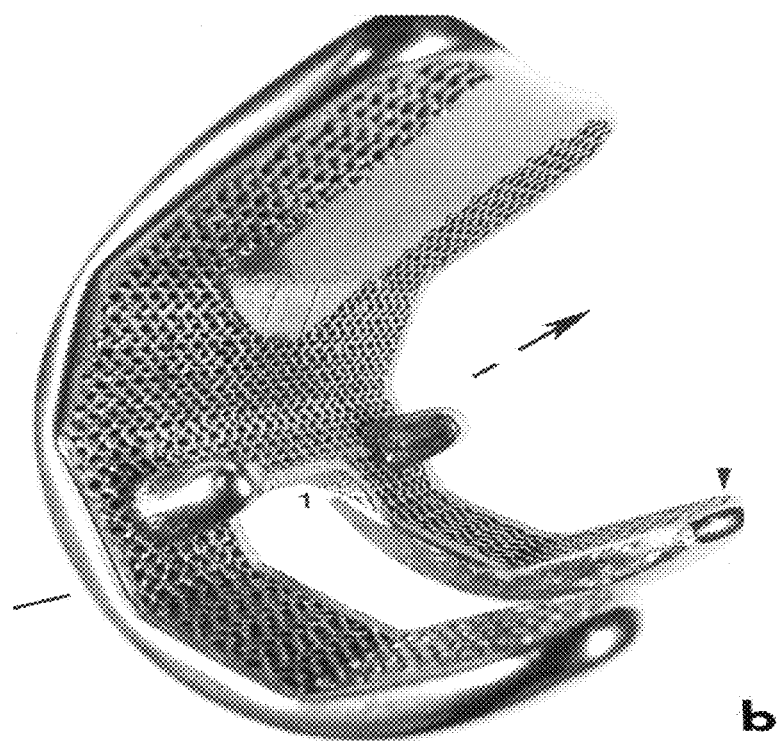
Figure 21C:
Figure 22A:
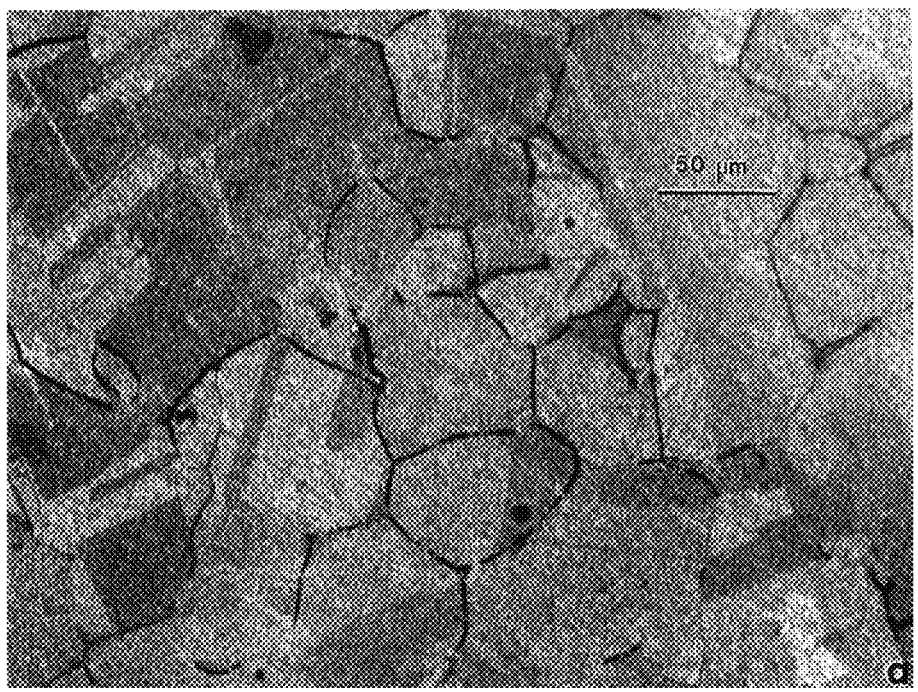
FIGS. 22A and 22B show optical metallography views for the cut section for the annealed and polished femoral (knee) component in FIG. 21B.
Figure 22B:
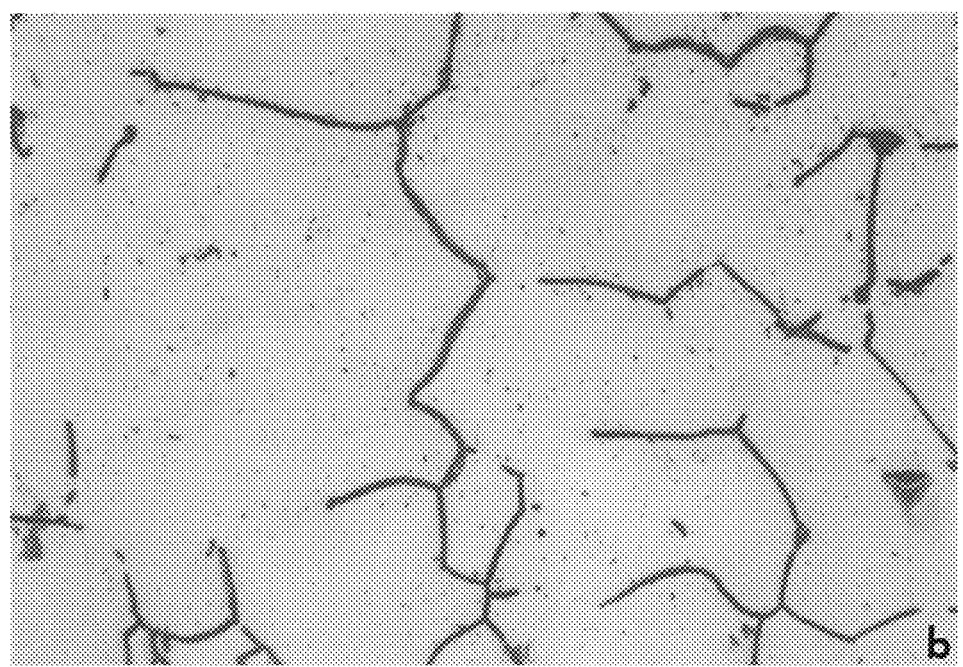
Figure 23:
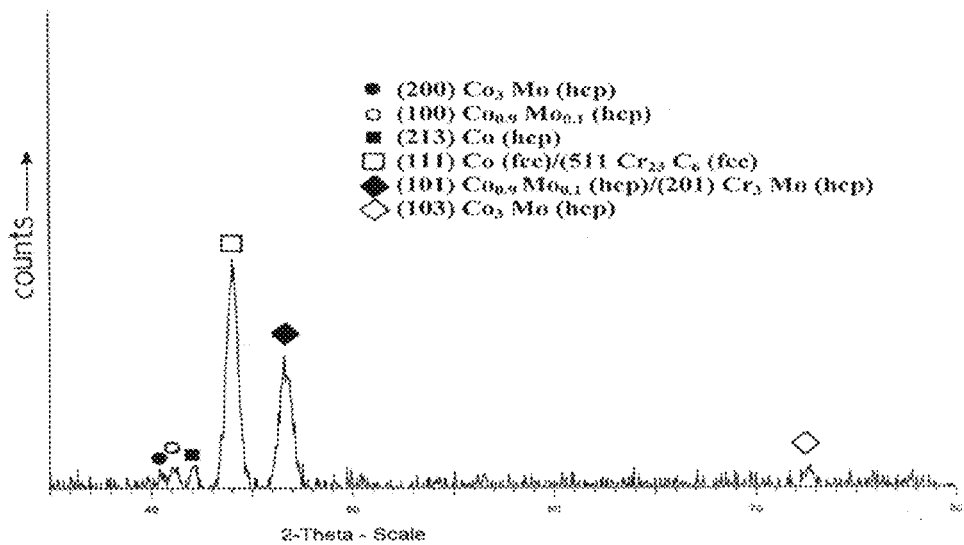
FIG. 23 shows the XRD pattern corresponding to the section cut from the annealed and polished femoral (knee) component in FIG. 21B. Indexed peaks are noted by keys.

Knee Component/Prototype Characterization: FIG. 19 shows an as-fabricated (EBM) femoral (knee) component prototype (FIGS. 19A and 19B) along with the corresponding SEM-EDS composition spectrum (FIG. 19C) which essentially matches the EDS spectrum for the original precursor Co—Cr—Mo powder shown in FIG. 9C. The larger arrow in FIG. 19B shows the corresponding build direction from left to right while the small arrow near the bottom of the image illustrates where test samples were cut for mounting, polishing and etching for optical metallography and hardness testing. FIG. 20A shows a typical view of the microstructure in this cut plane which, because of the build direction, would roughly correspond to the vertical plane for the cylindrical and block specimens illustrated in FIGS. 13-15. However, the microstructure in FIG. 20A and in a magnified view in FIG. 20B shows mixtures of columnar carbides and carbide arrays measuring roughly 2-3 µm as noted previously in the horizontal plane views for FIGS. 13 and 15. FIGS. 21A and 21B show views for the annealed and polished femoral (knee) component similar to FIGS. 19A and 19B, while FIG. 21C illustrates the placement of a commercial knee component in a total knee replacement, which also includes the tibial insert illustrated at "t" in FIG. 21C. In many commercial applications the tibial knee fixture is Ti-6Al-4V with a highly-crosslinked polyethylene block inserted on the upper table of this implant (not visible in the X-ray image of FIG. 21C. As in FIG. 19B, FIG. 21B illustrates the build direction by the larger arrow and the section from which a section was removed for analysis indicated by the smaller arrow. FIG. 22A shows a typical etched specimen from the plane section removed as illustrated at the small arrow in FIG. 21B, which shows a generally equiaxed fcc grain structure, containing numerous, coherent annealing twins, as well as concentrated, grain boundary carbides ($Cr_{23}C_6$) (FIG. 22B). The average grain dimension, not including annealing twin boundaries, was measured to be ~42 µm. These carbides, which can be preferentially etched at higher energy grain boundary segments, are illustrated in FIG. 22B. However, the high carbide fraction noted in FIGS. 13-15 and FIG. 20 is significantly reduced in the annealed knee component (FIG. 22). This is most apparent on comparing the XRD pattern for the as-fabricated cylinder in FIG. 16 with the annealed knee component pattern in FIG. 23, where the prominent (531) $Cr_{23}C_6$ carbide peak (in FIG. 16) is missing.

Figure 24A:
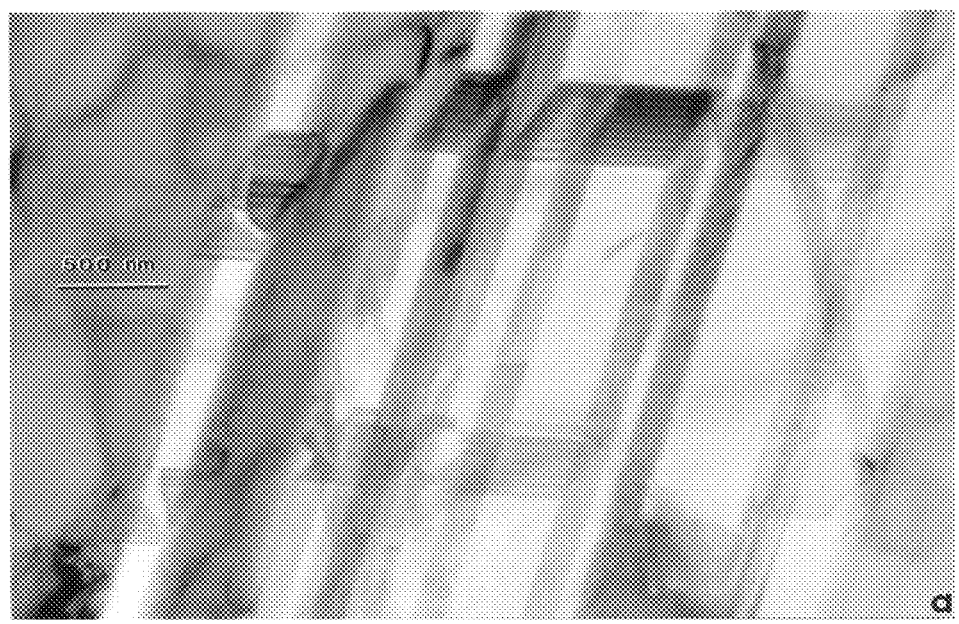
Figure 24B:
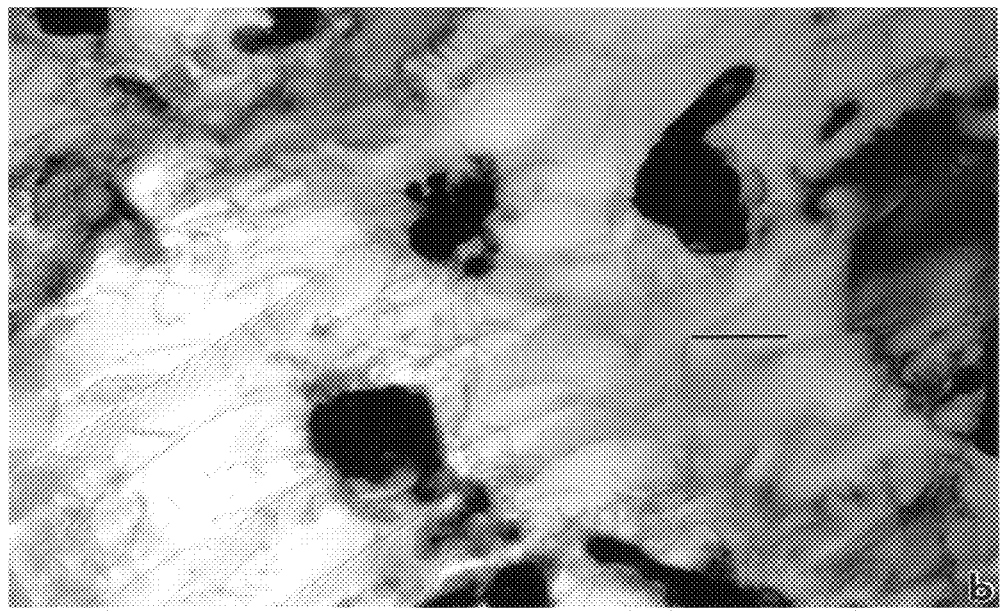
Figure 25:
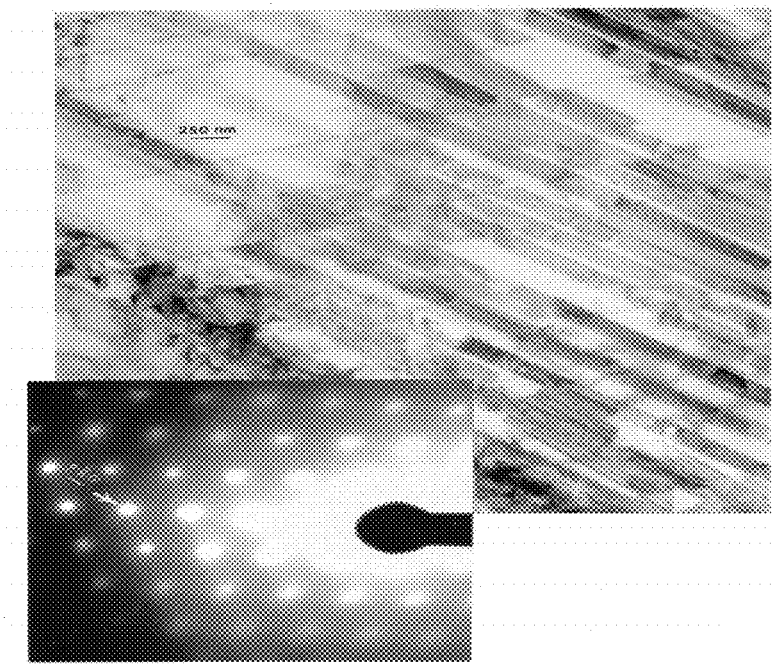
FIG. 25 is the TEM bright-field image showing high density of intrinsic stacking faults on (111) planes coincident with the [2 crystal direction shown in the SAED (110) pattern insert. Representative (110) grain in an annealed and polished femoral (knee) component shown in FIG. 21B.

While annealing at high temperature has dissolved a large fraction of the CoCr fcc matrix carbides (and cellular arrays of carbides) as shown on comparing FIGS. 20A and 20B with FIGS. 22A and 22B, the characteristic fcc stacking fault microstructures have not been altered as indicated in the comparative TEM images in FIG. 24. FIG. 24A shows stacking faults in an annealed knee component sample while FIG. 24B illustrates a corresponding TEM bright-field image for a cylindrical component horizontal plane sample as shown in FIG. 17. The stacking faults exhibit similar features in FIGS. 24A and 24B, while the as-fabricated and unannealed cylindrical specimen in FIG. 24B containing prominent $Cr_{23}C_6$ precipitates also contains a significantly higher dislocation density. Correspondingly there was a generally greater density of stacking faults in the annealed knee component as illustrated in FIG. 25. In contrast to FIG. 17, the SAED pattern insert in FIG. 25 shows no evidence of $Cr_{23}C_6$ carbides, and the (110) fcc SAED pattern exhibits a calculated lattice parameter of 3.55 Å; consistent with fcc Co.

In this context of microstructure variations for the as-fabricated (knee) component versus the annealed (knee) component (FIGS. 20 and 22), the corresponding hardness results supported the expected variation in mechanical properties. The microindentation hardness measurements (HV) and corresponding Rockwell C-scale (HRC) hardness values are shown for comparison in Table II which shows a 25% reduction in Vickers (HV) microhardness and 15% reduction in Rockwell C-scale (HRC) hardness after annealing.

Figures 26A, 26B:
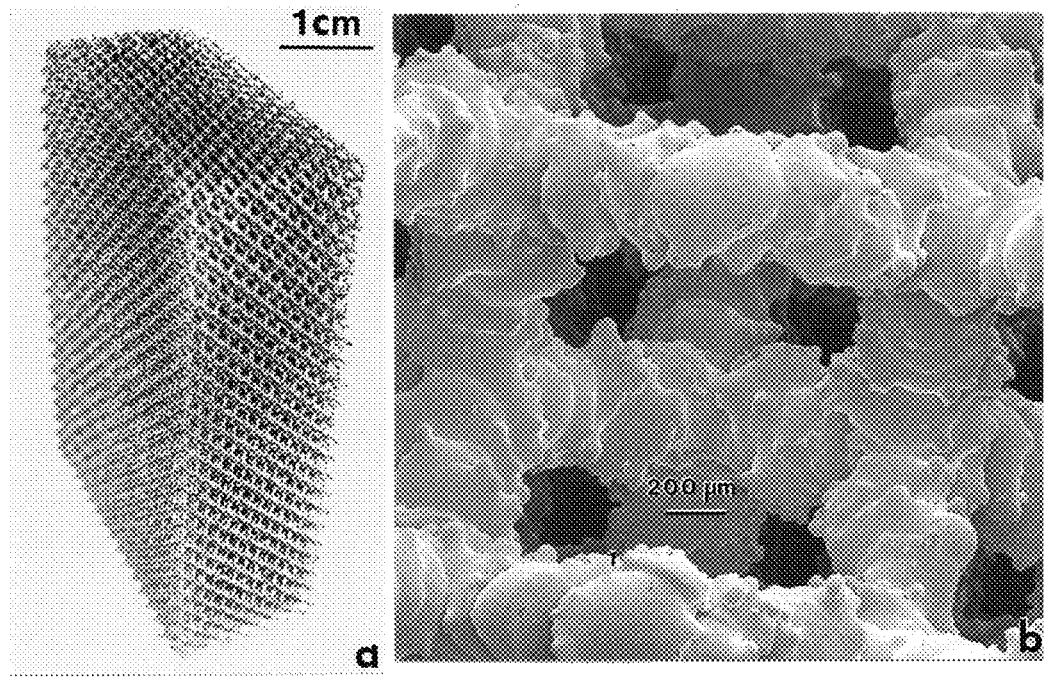
FIGS. 26A to 26C show reticulated Co—Cr—Mo mesh prototype fabricated by EBM.
Figure 26C:
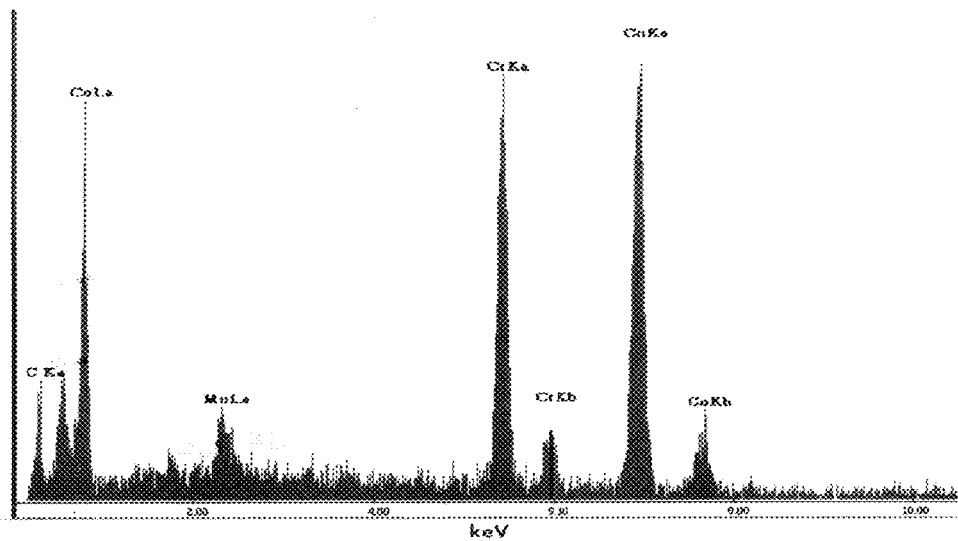

Mesh Component Characterization: FIG. 26A illustrates the as-fabricated Co—Cr—Mo mesh component while the microstructural features are shown in the SEM view of FIG. 26B. FIG. 26C shows the corresponding EDS spectrum which is essentially the same as that shown in FIG. 9C for the precursor powder, and FIG. 19C for the as-fabricated knee component. Quantitative comparisons for the Co—Cr—Mo components are also shown in Table I. This EBM fabricated mesh (FIG. 26A) had a density of 1.5 $g/cm^3$ in contrast to the fully dense cylindrical and rectangular block components with a density of 8.4 $g/cm^3$.

Figure 27:
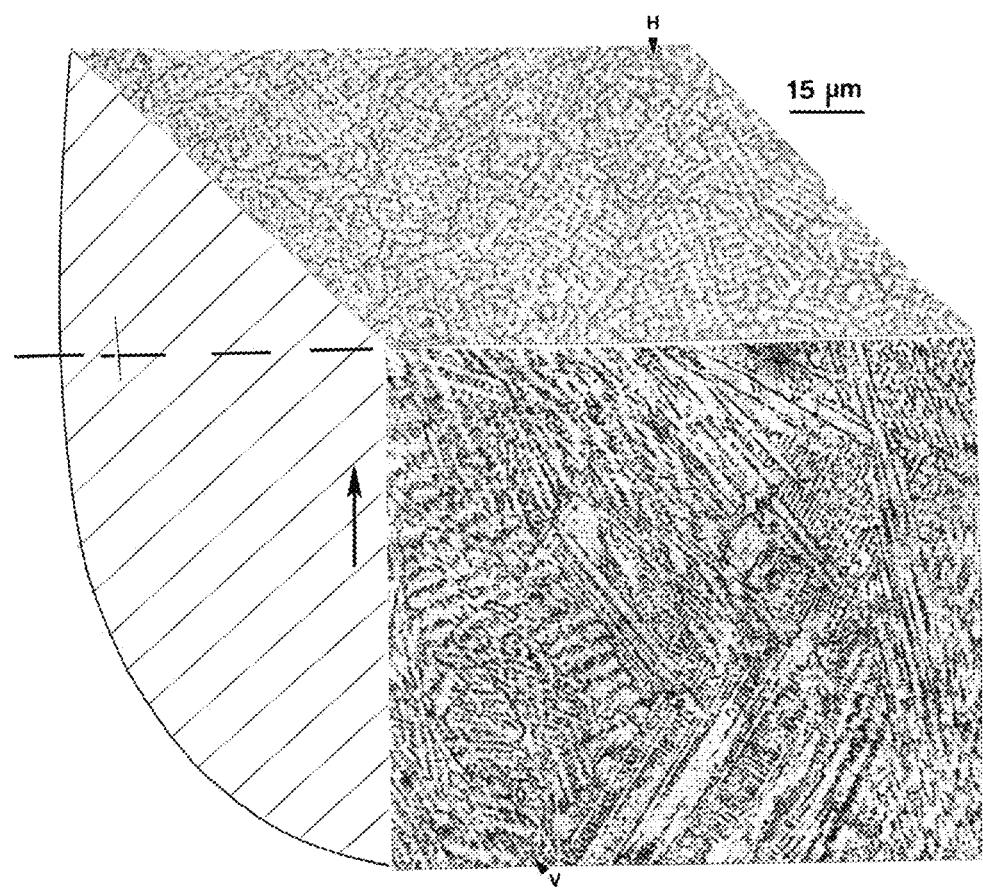
FIG. 27 are the optical metallography composite views for a mounted, polished, and etched mesh strut section from FIGS. 26A and 26B. (H) and (V) denote the horizontal and vertical planes relative to the cylindrical strut section and the build direction indicated by the large arrow.

The mesh sample shown in FIG. 26B was processed similar to extracted coupons which were mounted, ground, polished, and etched for optical metallography as described earlier. FIG. 27 illustrates the typical microstructures observed, which are similar to the carbide arrays observed in the composite horizontal and vertical plane views for the cylindrical and block components in FIGS. 13 and 15, respectively. However, unlike the cube-like carbide array in FIGS. 13 and 15, the carbides in FIG. 27 are often concentrated in slightly more concentrated and circular, cell-like arrays resembling sub-grain structures with dimensions of ~2 µm, similar to the more open, geometrical, cube-like (orthogonal) arrays in FIGS. 13 and 15. These arrays occur in part because of the circular element involved in building the cylindrical struts composing the mesh. The vertical plane component view shown in FIG. 27 is similar to but more irregular than, the cylindrical section illustrated in FIG. 14. As noted, the cylindrical geometry and the rapid solidification contribute to these more irregular carbide columns. As noted for comparison in Table II, the average microindentation hardness (HV) measured for these mesh struts was 6.8 GPa in the horizontal plane and 5.6 in the vertical plane, or roughly 25% harder than the as-fabricated, fully dense cylindrical and rectangular block components (FIGS. 13 and 15 respectively). This hardness difference for the Co—Cr—Mo mesh array (strut lengths in particular) in contrast to solid, fully dense components, is similar to Ti-6Al-4V mesh arrays in contrast to fully dense Ti-6Al-4V components, where the microindentation hardness difference varied from 31% to 75% [31]. The hardness and corresponding microstructure variations for mesh strut components is due in part to the rapid cooling rate during EBM fabrication in contrast to much slower cooling for larger EBM fabricated components (FIGS. 13 and 15 for example). These features have been observed for Ti-6Al-4V reticulated mesh structures [31] as well as cellular foams [32]. Moreover, there is an increase in the carbide precipitate fraction which contributes significantly to the hardness increase. In contrast to FIGS. 13-15A, this microstructural architecture illustrates the degree of control or variation implicit in electron beam scan rate variations and related beam induced solidification phenomena.

Co—Cr—Mo mesh prototypes represented by FIGS. 26A, 26B and 26C are a testament to the prospects for creating multi-functional, next generation biomedical components as previously demonstrated for Ti-6Al-4V mesh structures [31]. These porous surface structures can allow for effective bone cell ingrowth. A similar but more shallow mesh structure has been fabricated as a monolithic component as shown for the annealed and polished femoral (knee) prototype in FIG. 21B.

Figure 10C:
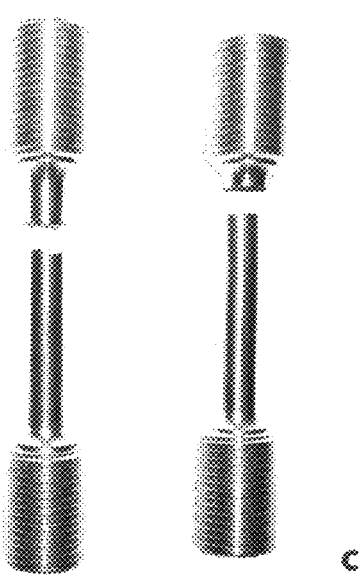

Mechanical Testing and Fractography: The tensile testing of two specimens prepared from as-fabricated cylindrical components as illustrated in FIGS. 10B and 10C produced average yield stress, UTS, and elongation measurements as noted for comparison in Table II. In contrast to the microindentation hardness (HV), the yield stress of 0.51 GPa is roughly half of that expected for many metals where yield stress ≅HV/3. However, while the yield stress is consistent with wrought and cast products, the UTS is considerably higher than as-cast or wrought ASTM F75 Co—Cr—Mo alloy where nominally the yield stress and UTS are 0.5 GPa and 0.9 GPa respectively. Correspondingly, as-cast Co—Cr—Mo (ASTM F75) alloy has an elongation <1% while wrought Co—Cr—Mo alloy has an elongation ~5%. These elongations compare to an average elongation of 3.6% for two tensile tests (FIG. 10C) (Table II), where the elongation ranged from 1.9% for one sample to 5.3% for the other.

Figure 28A:
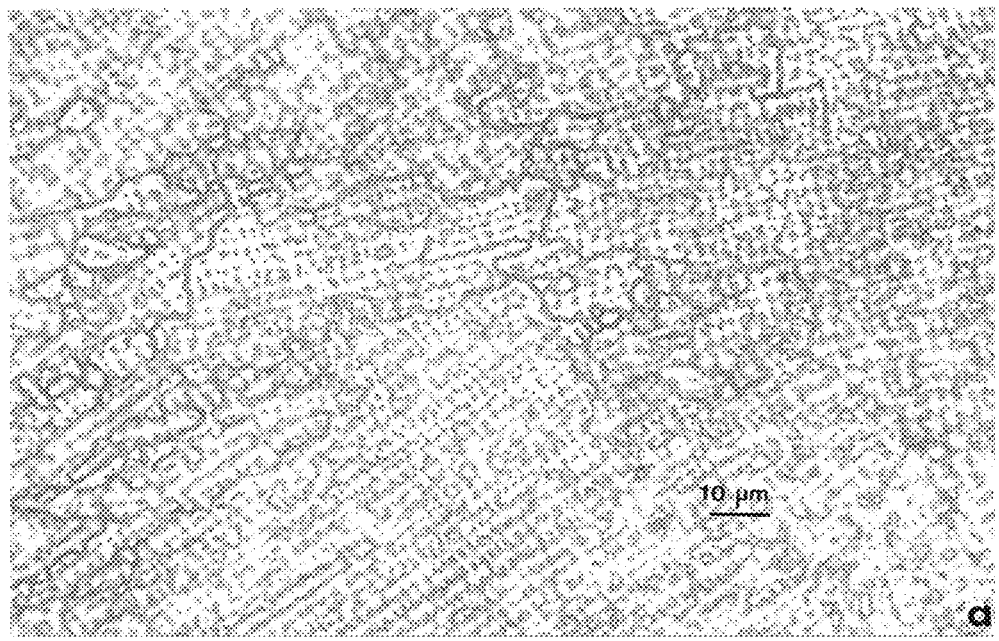
FIGS. 28A and 28B shows the optical metallography and SEM fractography comparison for cylindrical Co—Cr—Mo components represented in FIG. 10.
Figure 28B:
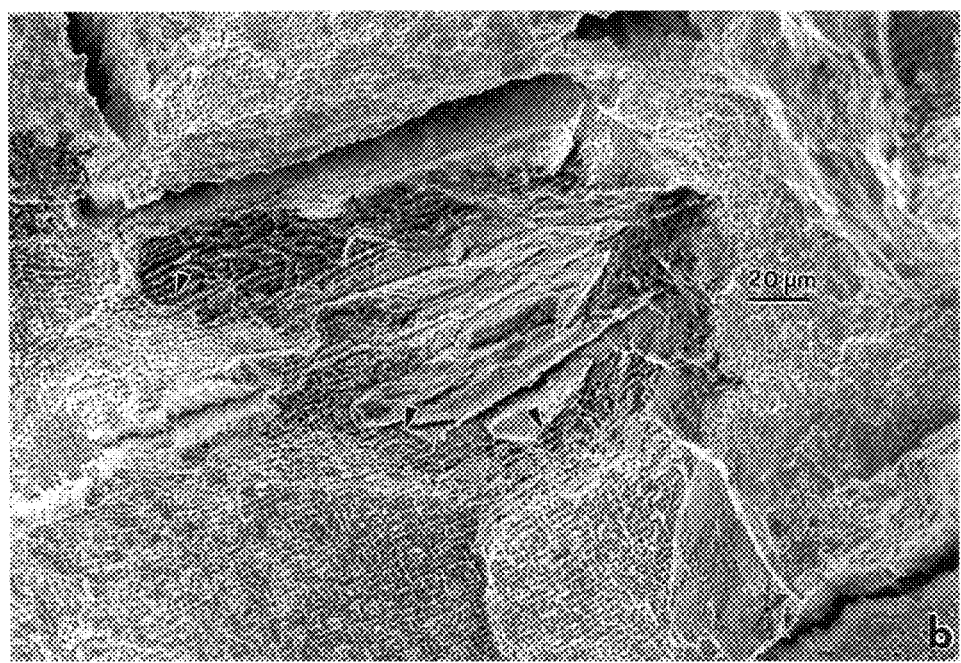
Figure 29A:
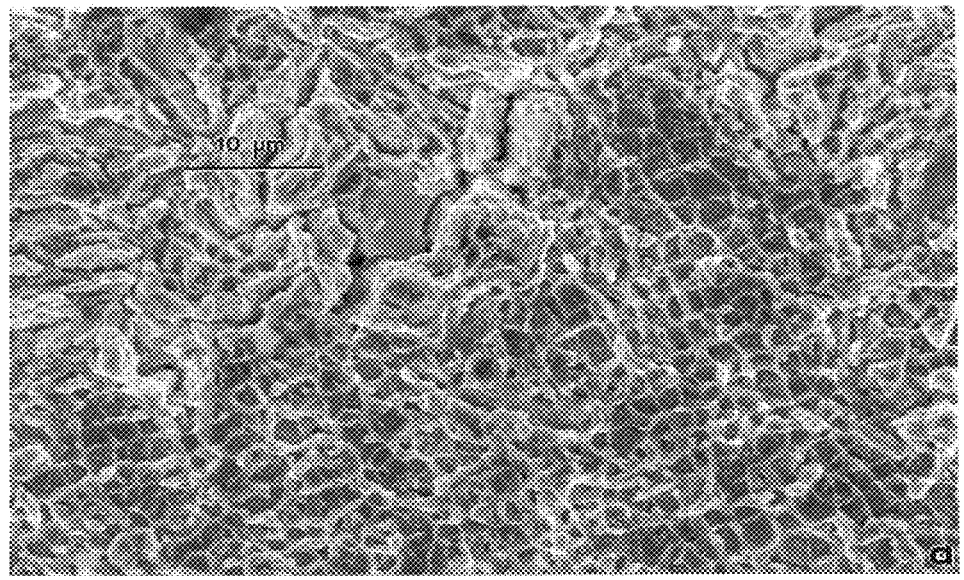
FIGS. 29A and 29B shows detailed (FIG. 29A) and magnified SEM fracture surface views (FIG. 29B) for the dimple arrays shown in FIG. 28B, (FIG. 29B) shows orthogonal-like dimple arrays which watch the carbide (cellular) arrays in the horizontal tensile specimen plane.
Figure 29B:
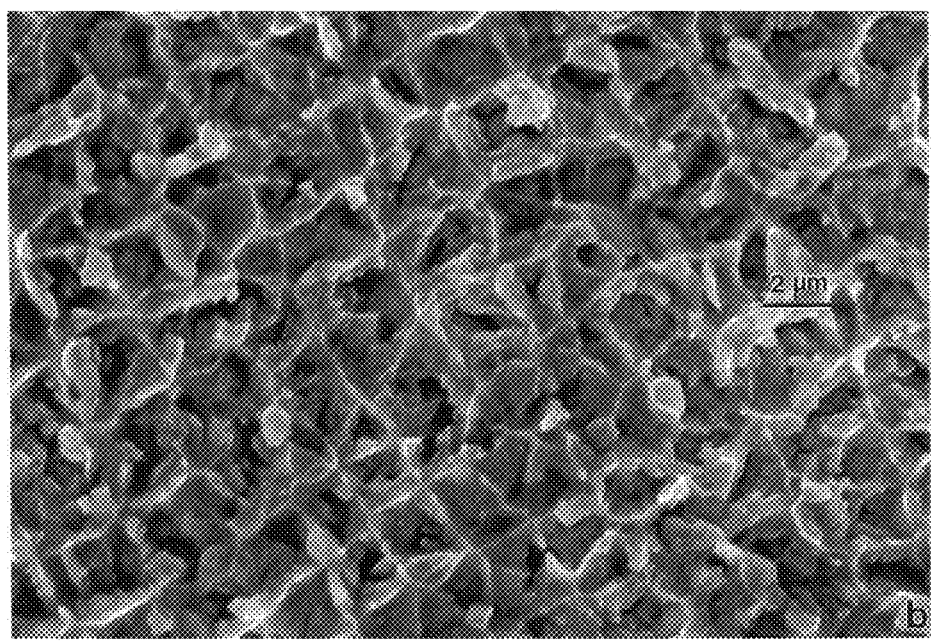

FIGS. 28A and 28B illustrate the horizontal plane optical metallographic microstructure (carbide arrays) in contrast to a similarly magnified and typical portion of the fracture surface for failed tensile specimens (FIG. 10C). Note that small ductile dimple arrays (arrows in FIG. 28B) essentially match the orthogonal carbide arrays in FIG. 28A. This fracture feature is even more prominently illustrated in the magnified SEM fractography images shown in FIGS. 29A and 29B.

The EBM fabrication of components and prototypes from Co-26Cr-6Mo-0.2C powder having a $Co_{0.8}Cr_{0.2}$ (hcp) crystal structure as described hereinabove creates Co-26Cr-6Mo-0.2C monoliths having an fcc CoCr matrix with CrMo phase components and unique, electron beam, scan-produced $Cr_{23}C_6$ fcc orthogonal carbide arrays when viewed perpendicular to the build direction, and carbide columns connected to these arrays when viewed in a plane parallel to the build direction. This is an example of a controlled microstructural architecture which can be altered with appropriate electron beam parameter and scanning variations. Correspondingly when these EBM fabricated prototypes are annealed, an equiaxed, fcc CoCr grain structure containing {111} coincident annealing twin forms with $Cr_{23}C_6$ carbides in predominantly high energy grain boundary portions. TEM bright-field observations of these annealed grains show a high density of intrinsic stacking faults on {111} planes, and essentially no matrix carbides.

The fracture surface microstructure for failed tensile specimens exhibited a unique, orthogonal ductile dimple cell structure which exactly matched the $Cr_{23}C_6$ carbide arrays observed in the as-fabricated cylinders from which the tensile specimens were machined. These microstructural features illustrate the unique nature of EBM fabrication of cobalt-base alloy products containing significant carbon, and the prospects for structure-property manipulation similar to commercial, cast Co-base alloys.

The ability to fabricate solid, fully dense and complex Co-26Cr-6Mo-0.2C monoliths as well as high strength, low-density reticulated mesh structures by EBM-additive manufacturing suggests that, like EBM fabricated Ti-6Al-4V products [31,32], multifunctional, complex monoliths having a wide range of mechanical properties can be produced with Co-base alloys. These monolithic components can include mesh or open cellular foam-coated biomedical devices for efficient bone cell ingrowth, impact energy absorbing arrays for aerospace or automotive applications, and a variety of thermal energy management systems.

Significant advances in the development and manufacture of more compatible biomedical implants may be achieved through layer manufacturing of monolithic mesh and solid (fully dense) components as well as different or graded monolithic mesh arrays accommodating mechanical biocompatibilities as well as biological compatibilities for bone.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

United States Patent Application No. 20070151961: Fabrication of an implantable medical device with a modified laser beam.
United States Patent Application No. 20090221898: Shaped surgical tool.
United States Patent Application No. 20090035448: Medical device coating by laser cladding.
1. Yaqwszemski M J, et al. (Eds.) (2004) Biomaterials in orthopedics: Marcel Dekker, Inc., New York
2. Gibson I (Ed.) (2005) Advanced manufacturing technology for medical applications. Wiley, London
3. Mayer B J, Lahey Jr P J, Weinberg E H, et al. (1978) Effects on intact femora of dogs of the application and removal of metal plates. A metabolic and structural study comparing stiffer and more flexible plates. J Bone Joint Surg Am 60:940-970
4. Oh I K, Nomora N, Hanada S (2003) Mechanical properties of porous titanium compacts prepared by powder sintering. Scripta Mater 49:197-202
5. Currey J D (2002) Bone-structure and mechanics. Princeton University Press, Princeton and Oxford
6. van Blitterswijk A, Grote J J, Kuijpers W et al. (1986) Macropore tissue ingrowth: a quantitative and qualitative study on hydroxyapatite ceramic. Biomaterials 7:137-143
7. Schliephake H, Neukam F W, Klosa D (1991) Influence of pore dimensions on bone ingrowth into porous hydroxylapatite blocks used as bone graft substitutes. A histometric study. Int J Oval Maxillofac Surg 20:53-58
8. Gibson L J, Ashby M F (1997) Cellular solids: structure and properties. Cambridge University Press, New York
9. Ashby M F, Evans A, Fleck N A, et al. (2000) Metal foams: a design guide. Butterworth-Heinemann, Boston Mass.
10. Davis N G, Teisen J, Schuh C, et al. (2001) Solid-state foaming of titanium by superplastic expansion of argon-filled pores. J Mater Res 16:1508-1509
11. Li J P, Li S H, de Groot K et al. (2002) Preparation and characterization of porous titanium. Key Eng Mater 218:51-54
12. Dunand D C (2004) Processing of titanium foams. Adv Engr Mater 6(6):369-376
13. Lefebvre L-P, Banhart J, Dunand D C (2008) Porous metals and metallic foams: current status and recent developments. Adv Engr Mater 10(9):775-787
14. Li Q, Che E, Bice D R, et al. (2008) Mechanical properties of cast Ti-6Al-4V lattice block structures. Metall & Mater Trans A 39A:441-449
15. Heinl P, Müller L, Körner C, et al. (2008) Cellular Ti-6Al-4V structures with interconnected macro porosity for bone implants fabricated by selective electron beam melting. Acta Biomaterialia 4:1536-1544
16. Murr L E, Esquivel E V, Quinones S A, et al. (2009) Microstructures and mechanical properties of electron beam—rapid manufactured Ti-6Al-4V biomedical prototypes compared to wrought Ti-6Al-4V. Mater. Characterization 60:96-105
17. T. C. Sims, N. S. Stoloff, W. C. Hagel (Eds.) Superalloys II, Wiley, New York, 1987
18. P. Crook, Cobalt, Cobalt alloys, in ASM Metal Handbook, vol. 2, Materials Park, Ohio, 1993, pp. 446-456
19. ASM International, Nickel, Colbalt and Their Alloys, Materials Park, Ohio, 2000
20. K. C. Antony, Wear-resistant cobalt base alloys, J. Metals 35 (1983) 52-60
21. S. Alamert, H. K. D. H. Bhadeshia, Comparison of the microstructure and abrasive wear properties of Stellite hardfacing alloys deposited by arc welding and laser cladding, Metals Technol. 20 (1989) 1037-1054
22. J. Shin, J. M. Doh, J. K. Yoon, D. Y. Lee, J. S. Kim, Effect of molybdenum on the microstructure and wear resistance of cobalt-base Stellite alloys, Surf. Coat. Technol. 166 (2003) 117-126
23. J. S. Garcia, M. A. Medrano, A. S. Rodriguez, Formation of hcp martensite during the isothermal aging of an fcc Co-27 Cr-5Mo-0.05C implant alloy, Metall. Mater. Trans. A30 (1999) 1177-1184
24. P. Huang, H. F. Lopez, A thermal-martensite in a Co—Cr—Mo alloy: grain size effects, Mater. Lett. 39 (1999) 244-248
25. T. M. Devine, J. Wulff, Cast versus wrought cobalt-chromium surgical implant alloys, J. Biomed. Mater. Res. 9 (2) (2004) 151-167
26. D. G. Poitout, Biomechanics and Biomaterials in Orthopaedics, Springer, N.Y., 2004
27. C. G. Meacock, R. Vilar, Structure and properties of a biomedical Co—Cr—Mo alloy produced by laser powder microdeposition, J. Laser Appl. 21 (2) (2009) 88-95
28. L. E. Murr, S. A. Quinones, S. M. Gaytan, M. I. Lopez, A. Rodela, E. Y. Martinez, D. H. Hernandez, E. Martinez, F. Medina, R. B. Wicker, Microstructure and mechanical behavior of Ti-6Al-4V for biomedical applications produced by rapid-layer manufacturing J. Mech. Behavior Biomed. Mater. 2 (2009) 20-32
29. L. E. Murr, S. M. Gaytan, M. I. Lopez, E. Martinez, F. Medina, R. B. Wicker, Metallographic Characterization of additive-layer manufactured products by electron beam melting, Practical Metall. XLVI. (2009) 442-453
30. S. M. Gaytan, L. E. Murr, F. Medina, E. Martinez, M. I. Lopez, R. B. Wicker, Advanced metal powder-based manufacturing of complex components by electron beam melting, Mater. Technol.: Adv. Perform. Mater. 24 (3) (2009) 180-190
31. L. E. Murr, S. M. Gaytan, F. Medina, H. Lopez, E. Martinez, D. H. Hernandez, L. Martinez, M. I. Lopez, R. B. Wicker, J. Bracke, Phil. Trans. Roy Soc. A, in press (2009)
32. L. E. Murr, S. M. Gaytan, F. Medina, E. Martinez, J. L. Martinez, D. H. Hernandez, B. I. Machado, D. A. Ramirez, R. B. Wicker, Characterization of Ti-6Al-4V open cellular foams fabricated by additive manufacturing using electron beam melting. Mater. Sci. Engng. A., in press (2009)
33. S. M. Gaytan, L. E. Murr, F. Medina, E. Martinez, J. L. Martinez, R. B. Wicker, Fabrication and characterization of reticulated, porous mesh arrays and foams for aerospace applications by additive manufacturing using electron beam melting, Global Innovations in manufacturing of Aerospace Materials, Proc. 11th MPMD (TMS) Global Innovations Symposium, to be published 2010
34. T. Kilner, R. M. Pilliar, G. C. Weatherly, C. Allibert, Phase identification and incipient melting in a Co—Cr surgical implant alloy, J. Biomed. Mater. Res. 16 (1982) 63-79.

35. M. Caudillo, M. Herrera-Trejo, M. R. Castro, E. Ramirez, C. R. Gonzalez, J. I. Juarez, On carbide dissolution in as-cast ASTM F75 alloy, *J. Biomed. Mater. Res.* 59(2) (2001) 378-385.

36. L. E. Murr, Interfacial Phenomena in Metals and Alloys, Addison-Wesley, New York, 1975. Reprinted by Tech Books, Herndon, Va., 1990 and available from CBLS.com.

What is claimed is:

1. A method of making a three dimensional structure comprising:
    designing a three-dimensional structure;
    melting the three-dimensional structure from two or more layers of a metal powder with an electron or a laser beam, wherein the position where the metal is melted into the structure is formed along a layer of metal powder, wherein a location and an intensity of the beam striking the metal layer is based on the three-dimensional structure and is controlled and directed by a processor; and
    removing the metal powder from the three-dimensional structure that is not melted, wherein the step of removing the metal powder further comprises the steps of:
        contacting the metal powder that is not melted with one or more ultrasonic devices; and
        removing the metal powder that is not melted by sonication using the one or more ultrasonic devices, wherein the sonication is a dry sonication.

2. The method of claim 1, wherein the one or more ultrasonic devices are selected from at least one of resonant probes, ultrasonic welders or high frequency sound transmission devices.

3. The method of claim 1, wherein the ultrasonic device is a resonant probe.

4. The method of claim 3, wherein the resonant probe is operated at frequencies ranging from 20 to 80 kHz.

5. The method of claim 1, wherein a frequency of operation of the one or more ultrasonic device is dependent on a shape, a density, and a geometry of the three-dimensional structure.

6. The method of claim 1, wherein the three dimensional structure comprises at least a portion that is a reticulated mesh array.

7. The method of claim 1, wherein the beam melts metal powder layers using electron or laser beams.

8. The method of claim 1, wherein the metal powder comprises Ti-6A1-4V.

9. The method of claim 1, wherein the metal powder comprises Co-26Cr-6Mo-0.2C.

10. The method of claim 1, wherein the three dimensional structure comprises at least one of a porous coating, a thin porous bead coating, a sintered mesh array, a thermal-spray coating, and a metallic foam on a medical device.

11. The method of claim 1, further comprising the steps of obtaining three-dimensional coordinates for a shape for tissue replacement, calculating the shape of a three-dimensional implant based on the three-dimensional coordinates of the shape for tissue replacement, and forming the three-dimensional implant.

12. The method of claim 1, further comprising the steps of obtaining three-dimensional coordinates for a shape for tissue replacement, calculating the shape of a three-dimensional implant based on the three-dimensional coordinates of the shape for tissue replacement, and selecting one or more metal powders to form the three-dimensional implant based on at least one of weight, mechanical strength, porosity, geometry and biocompatibility.

13. The method of claim 1, further comprising the step of adding one or more biocompatible polymers to the three dimensional structure.

14. The method of claim 1, further comprising the step of adding one or more cellular growth factors.

15. The method of claim 1, wherein the three dimensional structure comprises orthopedic implants, femoral stems, tibial stems, femoral rods, and combinations and modifications thereof.

16. A method of making a biologically compatible, three dimensional, mesh array comprising:
    designing a three-dimensional mesh array structure comprising lattice elements;
    melting the three-dimensional mesh array structure from two or more layers of a biocompatible metal powder with an electron beam, wherein a position where the metal is melted into the structure is formed along a layer of metal powder, wherein a location and an intensity of the beam striking the metal layer is based on the three-dimensional structure and is controlled and directed by a processor; and
    removing metal powder from the three-dimensional structure that is not melted, wherein the step of removing the metal powder further comprises the steps of:
        contacting the metal powder that is not melted with one or more ultrasonic devices; and
        removing the metal powder that is not melted by sonication using the one or more ultrasonic devices, wherein the sonication is a dry sonication.

17. The method of claim 16, wherein the one or more ultrasonic devices are selected from at least one of resonant probes, ultrasonic welders or high frequency sound transmission devices.

18. The method of claim 16, wherein the ultrasonic device is a resonant probe.

19. The method of claim 18, wherein the resonant probe is operated at frequencies ranging from 20 to 80 kHz.

20. The method of claim 16, wherein a frequency of operation of the one or more ultrasonic device is dependent on a shape, a density, and a geometry of the three dimensional reticulated mesh array.

21. The method of claim 16, wherein the metal powder comprises Ti-6A1-4V.

22. The method of claim 16, wherein the metal powder comprises Co-26Cr-6Mo-0.2C.

23. The method of claim 16, wherein the three dimensional structure comprises at least one of a porous coating, a thin, porous bead coating, a sintered mesh arrays, a thermal-spray coating, and a metallic foam on a medical device.

24. The method of claim 16, further comprising the steps of obtaining three-dimensional coordinates for a shape for tissue replacement, calculating the shape of a three-dimensional implant based on the three-dimensional coordinates of the shape for tissue replacement, and forming the three-dimensional implant.

25. The method of claim 16, further comprising the steps of obtaining three-dimensional coordinates for a shape for tissue replacement, calculating the shape of a three-dimensional implant based on the three-dimensional coordinates of the shape for tissue replacement, and selecting one or more metal powders to form the three-dimensional implant based on at least one of weight, mechanical strength, porosity, geometry and biocompatibility.

26. The method of claim 16, further comprising the step of adding one or more biocompatible polymers to the three dimensional structure.

27. The method of claim 16, further comprising the step of adding one or more cellular growth factors.

28. The method of claim 16, comprising the optional step of annealing and polishing the biologically compatible, three dimensional, reticulated mesh array.

* * * * *